(12) United States Patent
Ariel et al.

(10) Patent No.: US 9,850,278 B2
(45) Date of Patent: Dec. 26, 2017

(54) SYNTHETIC ANTI-INFLAMMATORY PEPTIDES AND USE THEREOF

(71) Applicant: CARMEL-HAIFA UNIVERSITY ECONOMIC CORP., Haifa (IL)

(72) Inventors: Amiram Ariel, Kiryat Motzkin (IL); Aviv Lutaty, Kiryat Ata (IL)

(73) Assignee: Carmel-Haifa University Economic Corp., Haifa (IL)

( * ) Notice: Subject to any disclaimer, the term of this patent is extended or adjusted under 35 U.S.C. 154(b) by 47 days.

(21) Appl. No.: 14/785,878

(22) PCT Filed: Apr. 23, 2014

(86) PCT No.: PCT/IL2014/050373
§ 371 (c)(1),
(2) Date: Oct. 21, 2015

(87) PCT Pub. No.: WO2014/174517
PCT Pub. Date: Oct. 30, 2014

(65) Prior Publication Data
US 2016/0075737 A1    Mar. 17, 2016

Related U.S. Application Data

(60) Provisional application No. 61/815,743, filed on Apr. 25, 2013.

(51) Int. Cl.
| | | |
|---|---|---|
| *C07K 5/087* | (2006.01) | |
| *C07K 14/47* | (2006.01) | |
| *C07K 7/06* | (2006.01) | |
| *C07K 14/79* | (2006.01) | |
| *C07K 4/12* | (2006.01) | |
| *C07K 7/08* | (2006.01) | |
| *A61K 38/00* | (2006.01) | |

(52) U.S. Cl.
CPC ............. *C07K 5/0812* (2013.01); *C07K 4/12* (2013.01); *C07K 7/06* (2013.01); *C07K 7/08* (2013.01); *C07K 14/4712* (2013.01); *C07K 14/79* (2013.01); *A61K 38/00* (2013.01); *A61L 2300/41* (2013.01); *Y10S 514/914* (2013.01)

(58) Field of Classification Search
CPC .... A61K 2300/00; A61K 38/00; A61K 38/04; A61K 38/1793; A61K 38/20; A61K 47/42; A61K 38/191; A61K 51/1021; A61K 38/19; C07K 16/244; C07K 16/2866; C07K 14/54; C07K 14/7155; G01N 33/6863; G01N 2333/4703; G01N 2333/54; G01N 2800/085; G01N 2800/12; G01N 33/5432; G01N 2800/382; G01N 2800/56; G01N 2800/7095; G01N 33/5067; G01N 33/6869

See application file for complete search history.

(56) References Cited

U.S. PATENT DOCUMENTS

| | | |
|---|---|---|
| 5,840,513 A | 11/1998 | Schubert |
| 5,856,444 A | 1/1999 | Kawakita |
| 6,165,730 A | 12/2000 | De Leys |
| 6,303,339 B1 | 10/2001 | Sontheimer |
| 6,531,130 B1 | 3/2003 | Steinman |
| 6,607,727 B1 | 8/2003 | Chisari |
| 6,660,842 B1 | 12/2003 | Saellberg |
| 6,664,230 B1 | 12/2003 | Fogelman |
| 7,338,929 B2 | 3/2008 | Debinski |
| 7,579,436 B2 | 8/2009 | Shih |
| 7,635,480 B2 | 12/2009 | Andre-Fontaine |
| 8,148,322 B2 | 4/2012 | Szeto |
| 2007/0197426 A1 | 8/2007 | Komine |
| 2008/0293639 A1 | 11/2008 | Fogelman |
| 2009/0097811 A1 * | 4/2009 | Hadzialic ............... B82Y 20/00 385/131 |
| 2010/0240598 A1 * | 9/2010 | Fogelman .......... C07K 5/06078 514/21.3 |
| 2012/0021970 A1 | 1/2012 | Schiller |

FOREIGN PATENT DOCUMENTS

| | | | |
|---|---|---|---|
| EP | 0445801 | 9/1991 | |
| EP | 0852234 | 7/1998 | |
| EP | 2305283 A1 * | 4/2011 | ............. A61K 38/10 |
| JP | 2003289749 | 10/2003 | |
| JP | 2004155751 | 6/2004 | |
| JP | 2011006468 | 1/2011 | |

(Continued)

OTHER PUBLICATIONS

Datta et al., (2004) Aromatic residue position on the nonpolar face of class a amphipathic helical peptides determines biological activity. J Biol Chem 279(25): 26509-17.

Kanyshkova et al., (2001) Lactoferrin and its biological functions. Biochemistry (Mosc) 66(1): 1-7.

Komine et al., (2005) Small molecule lactoferrin with an inflammatory effect but no apparent antibacterial activity in mastitic mammary gland secretion. J Vet Med Sci 67(7): 667-77.

Komine et al., (2006) Effect of combination therapy with lactoferrin and antibiotics against staphylococcal mastitis on drying cows. J Vet Med Sci 68(3): 205-11.

(Continued)

*Primary Examiner* — Satyanarayana R Gudibande
*Assistant Examiner* — Jia-Hai Lee
(74) *Attorney, Agent, or Firm* — Roach Brown McCarthy & Gruber, P.C.; Kevin D. McCarthy

(57) ABSTRACT

The present invention is directed to synthetic anti-inflammatory peptides and use thereof in the treatment and prevention of inflammatory and fibrotic conditions. Specifically, the invention relates in some embodiments to short isolated peptides having the amino acid sequence Phe-Lys-Glu (FKE), Tyr-Lys-Glu (YKE) or comprising a plurality of these sequences that may be flanked by Ala/Gly (A/G) linkers. The invention further relates in some embodiments to methods for inhibiting scar formation and for treating and alleviating IL-10 dependent conditions.

12 Claims, 8 Drawing Sheets

(56) References Cited

FOREIGN PATENT DOCUMENTS

| WO | 95/16462 | 6/1995 | | |
|---|---|---|---|---|
| WO | 95/29938 | 11/1995 | | |
| WO | 97/48728 | 12/1997 | | |
| WO | 98/10787 A2 | 3/1998 | | |
| WO | 98/10792 A1 | 3/1998 | | |
| WO | 99/57144 | 11/1999 | | |
| WO | 00/01730 | 1/2000 | | |
| WO | 03/103572 | 12/2003 | | |
| WO | WO2008028692 A2 * | 3/2008 | ............ | G01N 33/50 |
| WO | 2009/027768 | 3/2009 | | |
| WO | 2009/062898 | 5/2009 | | |
| WO | 2012/174117 | 12/2012 | | |
| WO | 2013/014669 | 1/2013 | | |

OTHER PUBLICATIONS

Komine et al., (2006) Inflammatory effect of cleaved bovine lactoferrin by elastase on staphylococcal mastitis. J Vet Med Sci 68(7): 715-23.

Komine et al., (2007) Cleaved inflammatory lactoferrin peptides in parotid saliva of periodontitis patients. Mol Immunol 44(7): 1498-508.

Krönke et al., (2012) The 12/15-lipoxygenase pathway counteracts fibroblast activation and experimental fibrosis. Ann Rheum Dis 71(6): 1081-7.

Lim et al., (2008) A cyclic RGD-coated peptide nanoribbon as a selective intracellular nanocarrier. Org Biomol Chem 6(11): 1944-8.

Pisarev et al., (2003) Full-length dominant-negative survivin for cancer immunotherapy. Clin Cancer Res 9(17): 6523-33.

Vogel et al., (2002) Towards a structure-function analysis of bovine lactoferricin and related tryptophan- and arginine-containing peptides. Biochem Cell Biol 80(1): 49-63.

Singh et al., (2005) Development of an in vitro screening assay to test the antiinflammatory properties of dietary supplements and pharmacologic agents. Clin Chem 51(12): 2252-6 (5 pages).

Slootstra et al., (1996) Structural aspects of antibody-antigen interaction revealed through small random peptide libraries. Mol Divers 1(2): 87-96 (10 pages).

* cited by examiner

SEQUENCE LISTING

```
<160> NUMBER OF SEQ ID NOS: 21

<210> SEQ ID NO 1
<211> LENGTH: 3
<212> TYPE: PRT
<213> ORGANISM: Artificial Sequence
<220> FEATURE:
<223> OTHER INFORMATION: Peptide

<400> SEQUENCE: 1

Phe Lys Glu
1

<210> SEQ ID NO 2
<211> LENGTH: 3
<212> TYPE: PRT
<213> ORGANISM: Artificial Sequence
<220> FEATURE:
<223> OTHER INFORMATION: Peptide

<400> SEQUENCE: 2

Tyr Lys Glu
1

<210> SEQ ID NO 3
<211> LENGTH: 3
<212> TYPE: PRT
<213> ORGANISM: Artificial Sequence
<220> FEATURE:
<223> OTHER INFORMATION: Peptide

<400> SEQUENCE: 3

Phe Lys Asp
1

<210> SEQ ID NO 4
```

```
<211> LENGTH: 5
<212> TYPE: PRT
<213> ORGANISM: Artificial Sequence
<220> FEATURE:
<223> OTHER INFORMATION: Peptide

<400> SEQUENCE: 4

Phe Lys Glu Cys His
1               5

<210> SEQ ID NO 5
<211> LENGTH: 35
<212> TYPE: PRT
<213> ORGANISM: Artificial Sequence
<220> FEATURE:
<223> OTHER INFORMATION: Peptide

<400> SEQUENCE: 5

Phe Lys Glu Ala Ala Ala Ala Ala Phe Lys Glu Ala Ala Ala Ala Ala
1               5                   10                  15

Phe Lys Glu Ala Ala Ala Ala Ala Phe Lys Glu Ala Ala Ala Ala Ala
            20                  25                  30

Phe Lys Glu
        35

<210> SEQ ID NO 6
<211> LENGTH: 35
<212> TYPE: PRT
<213> ORGANISM: Artificial Sequence
<220> FEATURE:
<223> OTHER INFORMATION: Peptide

<400> SEQUENCE: 6

Phe Lys Glu Gly Gly Gly Gly Gly Phe Lys Glu Gly Gly Gly Gly Gly
1               5                   10                  15

Phe Lys Glu Gly Gly Gly Gly Gly Phe Lys Glu Gly Gly Gly Gly Gly
            20                  25                  30

Phe Lys Glu
        35

<210> SEQ ID NO 7
<211> LENGTH: 3
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminal acetyl group
<220> FEATURE:
<221> NAME/KEY: MISC_FEATURE
<222> LOCATION: (3)..(3)
<223> OTHER INFORMATION: C-terminal amide group

<400> SEQUENCE: 7

Phe Lys Glu
1

<210> SEQ ID NO 8
<211> LENGTH: 29
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
```

```
<222> LOCATION: (1)..(1)
<223> OTHER INFORMATION: N-terminal acetyl group
<220> FEATURE:
<221> NAME/KEY: MISC_FEATURE
<222> LOCATION: (4)..(4)
<223> OTHER INFORMATION: C-terminal amide group

<400> SEQUENCE: 8

Ala Ala Ala Ala Ala Phe Lys Glu Ala Ala Ala Ala Ala Phe Lys Glu
1               5                   10                  15

Ala Ala Ala Ala Ala Phe Lys Glu Ala Ala Ala Ala Ala
            20                  25

<210> SEQ ID NO 9
<211> LENGTH: 7
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: X1 is an amino acid, a peptide of 2 to 7 amino
      acids other than YR and LDH, a chemical derivatizing group or is
      absent
<220> FEATURE:
<221> NAME/KEY: MISC_FEATURE
<222> LOCATION: (2)..(2)
<223> OTHER INFORMATION: X2 is an amino acid other than K and R, a
      spacer of 2 to 7 amino acids comprising a plurality of A and/or G
      residues, or is absent
<220> FEATURE:
<221> NAME/KEY: MISC_FEATURE
<222> LOCATION: (6)..(6)
<223> OTHER INFORMATION: X3 is an amino acid other than V, K and R, a
      spacer of 2 to 7 amino acids comprising a plurality of A and/or G
      residues, or is absent
<220> FEATURE:
<221> NAME/KEY: MISC_FEATURE
<222> LOCATION: (7)..(7)
<223> OTHER INFORMATION: X4 is an amino acid, a peptide of 2 to 7 amino
      acids, a chemical derivatizing group or is absent, when X3 is
      absent, X4 is not HWR, LEG, LEGWEP, CTV, CTVEY, CTVEYEL, CHL, CHLA
      or HLA

<400> SEQUENCE: 9

Xaa Xaa Phe Lys Glu Xaa Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic peptide of formula Ib
<220> FEATURE:
<221> NAME/KEY: misc_feature
<222> LOCATION: (1)..(1)
<223> OTHER INFORMATION: X1 is an amino acid, a peptide of 2 to 7 amino
      acids, a chemical derivatizing group or is absent
<220> FEATURE:
<221> NAME/KEY: misc_feature
<222> LOCATION: (2)..(2)
<223> OTHER INFORMATION: X2 is an amino acid, a spacer of 2 to 7 amino
      acids comprising a plurality of A and/or G residues, or is absent
<220> FEATURE:
<221> NAME/KEY: misc_feature
<222> LOCATION: (2)..(6)
<223> OTHER INFORMATION: the peptide is provided with the proviso that
      X3-F-K-E-X4 are repeated 2-5 times
<220> FEATURE:
<221> NAME/KEY: misc_feature
<222> LOCATION: (2)..(6)
<223> OTHER INFORMATION: the peptide of Formula Ib is provided with the
``` proviso that X3-F-K-E-X4 is repeated 2-5 times
<220> FEATURE:
<221> NAME/KEY: misc_feature
<222> LOCATION: (6)..(6)
<223> OTHER INFORMATION: X3 is an amino acid, a spacer of 2 to 7 amino
      acids comprising a plurality of A and/or G residues, or is absent
<220> FEATURE:
<221> NAME/KEY: misc_feature
<222> LOCATION: (7)..(7)
<223> OTHER INFORMATION: X4 is an amino acid, a peptide of 2 to 7 amino
      acids, a chemical derivatizing group or is absent

<400> SEQUENCE: 10

Xaa Xaa Phe Lys Glu Xaa Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: X1 is an amino acid, a peptide of 2-7 amino
      acids other than RR, MDIDP, and KKNWIQ, a chemical derivatizing
      group or is absent
<220> FEATURE:
<221> NAME/KEY: MISC_FEATURE
<222> LOCATION: (2)..(2)
<223> OTHER INFORMATION: X2 is an amino acid, a spacer of 2-7 amino
      acids comprising a plurality of A and/or G residues, or is absent;
      wherein when X1 is absent and X2 is an amino acid, X2 is not Y or
      E
<220> FEATURE:
<221> NAME/KEY: MISC_FEATURE
<222> LOCATION: (6)..(6)
<223> OTHER INFORMATION: X3 is an amino acid, a spacer of 2-7 amino
      acids comprising a plurality of A and/or G residues, or is absent;
      wherein X4 is absent and X3 is an amino acid, X3 is not Y
<220> FEATURE:
<221> NAME/KEY: MISC_FEATURE
<222> LOCATION: (7)..(7)
<223> OTHER INFORMATION: X4 is an amino acid, a peptide of 2 to 7 amino
      acids, a chemical derivatizing group or is absent; wherein when X3
      is absent, X4 is not KEK

<400> SEQUENCE: 11

Xaa Xaa Tyr Lys Glu Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic peptide of formula IIb
<220> FEATURE:
<221> NAME/KEY: MISC_FEATURE
<222> LOCATION: (1)..(1)
<223> OTHER INFORMATION: X1 is an amino acid, a peptide of 2-7 amino
      acids, a chemical derivatizing group or is absent
<220> FEATURE:
<221> NAME/KEY: MISC_FEATURE
<222> LOCATION: (2)..(2)
<223> OTHER INFORMATION: X2 is an amino acid, a spacer of 2-7 amino
      acids comprising a plurality of A and/or G residues, or is absent
<220> FEATURE:
<221> NAME/KEY: MISC_FEATURE
<222> LOCATION: (2)..(6)
<223> OTHER INFORMATION: the peptide of formula IIb is provided with the
      proviso that the sequence X2-Y-K-E-X3 is repeated 2-5 times
<220> FEATURE:
<221> NAME/KEY: MISC_FEATURE

```
<222> LOCATION: (2)..(6)
<223> OTHER INFORMATION: the peptide of formula IIb is provided with the
      proviso that X2-Y-K-E-X3 is repeated 2-5 times
<220> FEATURE:
<221> NAME/KEY: MISC_FEATURE
<222> LOCATION: (6)..(6)
<223> OTHER INFORMATION: X3 is an amino acid, a spacer of 2-7 amino
      acids comprising a plurality of A and/or G residues, or is absent
<220> FEATURE:
<221> NAME/KEY: MISC_FEATURE
<222> LOCATION: (7)..(7)
<223> OTHER INFORMATION: X4 is an amino acid, a peptide of 2-7 amino
      acids, a chemical derivatizing group or is absent

<400> SEQUENCE: 12

Xaa Xaa Tyr Lys Glu Xaa Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: Peptide

<400> SEQUENCE: 13

Leu Glu Gly Trp Glu Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Peptide

<400> SEQUENCE: 14

Cys Thr Val Glu Tyr
1               5

<210> SEQ ID NO 15
<211> LENGTH: 7
<212> TYPE: PRT
<213> ORGANISM: Artificial Sequence
<220> FEATURE:
<223> OTHER INFORMATION: Peptide

<400> SEQUENCE: 15

Cys Thr Val Glu Tyr Glu Leu
1               5

<210> SEQ ID NO 16
<211> LENGTH: 4
<212> TYPE: PRT
<213> ORGANISM: Artificial Sequence
<220> FEATURE:
<223> OTHER INFORMATION: Peptide

<400> SEQUENCE: 16

Cys His Leu Ala
1

<210> SEQ ID NO 17
<211> LENGTH: 4
<212> TYPE: PRT
<213> ORGANISM: Artificial Sequence
<220> FEATURE:
<223> OTHER INFORMATION: Peptide
```

```
<400> SEQUENCE: 17

Ser Leu Asp His
1

<210> SEQ ID NO 18
<211> LENGTH: 5
<212> TYPE: PRT
<213> ORGANISM: Artificial Sequence
<220> FEATURE:
<223> OTHER INFORMATION: Peptide

<400> SEQUENCE: 18

Met Asp Ile Asp Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Peptide

<400> SEQUENCE: 19

Lys Lys Asn Trp Ile Gln
1               5

<210> SEQ ID NO 20
<211> LENGTH: 5
<212> TYPE: PRT
<213> ORGANISM: Artificial Sequence
<220> FEATURE:
<223> OTHER INFORMATION: Peptide

<400> SEQUENCE: 20

Glu Arg His Asn Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Peptide

<400> SEQUENCE: 21

Phe Lys Glu Cys His Leu Ala
1               5
```

SYNTHETIC ANTI-INFLAMMATORY PEPTIDES AND USE THEREOF

FIELD OF THE INVENTION

The present invention is directed to synthetic peptides useful for the treatment of inflammatory and fibrotic diseases.

BACKGROUND OF THE INVENTION

Inflammation is a biological response to injury, infection or irritation in which a cascade of cellular and microvascular reactions serves to eradicate the infection, remove damaged tissue and generate new tissue. During inflammation, stromal cells regulate leukocyte recruitment and survival through the secretion of specific chemokines and cytokines. Elimination of the cells and mediators that took part in the inflammatory response is essential for the eventual clearance or resolution of inflammation. Disruption of this homeostasis can lead to chronic inflammation and its corollary of severe illnesses, such as tissue fibrosis. Aberrations in immune responses may also lead to the development of autoimmune diseases, characterized by chronic, detrimental immune reactions in which the host's immune system attacks the host's own tissues.

Fibrosis defines the formation of excess fibrous connective tissue during the reparative and reactive process following tissue damage and inflammation. As major components of fibrosis, pro-fibrotic stromal cells play a critical role in the maintenance of chronic inflammation and often preclude full organ recovery, and in some cases can induce organ failure. This can lead to severe illnesses of major impact on public health such as liver cirrhosis, scleroderma, heart and pulmonary fibrosis, atherosclerosis and asthma, as well as skin fibrosis and scarring. The formation of tissue fibrosis is currently considered to be an irreversible process, which is poorly modulated by anti-inflammatory and immunosuppressive drugs. The mechanisms leading to the formation of tissue fibrosis has remained elusive and therefore has prevented the elaboration of an adequate therapeutic treatment. Nevertheless, it is currently appreciated that macrophages, due to their plastic properties, play indispensable roles at both the initiation of fibrosis and its prevention, through the coordination of the resolution of inflammation and balanced wound healing.

Among the various factors found to take part in inflammatory processes is the 80 kDa iron-binding glycoprotein lactoferrin. This glycoprotein represents one of the first defense systems against pathogens, exhibiting antimicrobial, antibacterial, antiviral and antiparasitic activities. Lactoferrin was also found to influence immune system cells both positively and negatively. On one hand, it has been reported to support proliferation, differentiation and activation of immune cells, and strengthen the immune response. On the other hand, lactoferrin has also been reported to have anti-inflammatory properties, in reducing the production of some pro-inflammatory cytokines such as tumor necrosis factor alpha (TNF-α), interleukin 1 beta (IL-1β) and interleukin 6 (IL-6), among others. In addition, lactoferrin has been reported to mediate inhibition of tumor growth and to possess several other biologic activities, including a ribonuclease activity (capable of RNA hydrolysis) and an osteogenic activity (Kanyshkova et al. Biochemistry 2001, 66(1): 1-7).

With the exception of iron binding, the biological activities of lactoferrin are considered to reside in a highly basic domain in the N-terminal region, designated lactoferricin. This part of the protein is released in the stomach at acidic pH by pepsin. Bovine lactoferricin is a highly potent 25aa peptide corresponding to residues 17-41 of lactoferrin, whereas the fragment released from human lactoferrin is larger (including positions 1-41) and has weaker antimicrobial properties. A number of lactoferricin derivatives have been described and tested, which retain at least a part of the activities of the native domain. An antimicrobial peptide derived from ovotransferrin, called OTAP-92, has also been identified, corresponding to positions 109-200 of ovotransferrin (Vogel et al., Biochem Cell Biol. 2002; 80(1):49-63).

Various other lactoferrin fragments were disclosed e.g. by US 2007/0197426, JP 2003/289749, JP 2011006468 and several additional publications to Komine et al. (Mol Immunol. 2007 March; 44(7):1498-508, J Vet Med Sci. 2006 July; 68(7):715-23, J Vet Med Sci. 2006 March; 68(3):205-11 and J Vet Med Sci. 2005 July; 67(7):667-77). These fragments were reported to encompass pro-inflammatory activities. Some of the pro-inflammatory activities of these fragments were suggested to reside within the amino acid sequence phenylalanine-lysine-aspartic acid (FKD), since two of four short synthetic peptides derived from these fragments, namely FKDCHLA and GQKDLLFKDSAI (pep1 and pep4, corresponding to positions 243-249 and 295-307 of human lactoferrin, respectively), demonstrated an inflammation-promoting activity and induction of pro-inflammatory cytokines and chemokines (TNF-α, IL-6, IL-8 and MCP-1). The Komine publications further examined the corresponding bovine synthetic peptides, and reported that bovine pep4 (GQRDLFKDSAL) induced the secretion of TNF-α, IL-6, IL-8 and MCP-1 from bovine mammary gland epithelial lined cells (BMEC), as did its human counterpart; however, bovine pep1 (FK<u>E</u>CHLA), differing from human pep1 by replacement of only one amino acid, was found inactive in this system.

Japanese Patent Application Publication No. JP 2004155751 discloses a peptide capable of suppressing the production of inflammatory cytokines such as TNF-α and IL-6, wherein the peptide used may be bovine lactoferrin hydrolyzed with a protease. The publication does not disclose peptides having the sequences FKD or FKE.

WO 2013/014669 to some of the inventors of the present invention discloses lactoferrin fragments of 15, 17 and 23 kDa that are characteristic of inflammation during various stages including resolution. Some of the polypeptide fragments encompass inter alia an FKD and/or FKE sequence. The publication discloses the use of lactoferrin fragments as diagnostic biomarkers for assessing the presence or absence of resolving inflammation and for monitoring the progression of inflammatory resolution in a subject.

Lim et al. (Org. Biomol. Chem., 2008, 6, 1944-1948) refer to an "RGD-FKE" nanoribbon, formed from a cyclic RGD integrin binding motif linked to an oligo-FKFE (Phe-Lys-Phe-Glu) sequence, reported to form a beta strand structure.

Pisarev et al. (Clin Cancer Res 2003; 9:6523-6533) disclose survivin-derived epitopes reactive with immune cells isolated from survivin-immunized subjects, inter alia FKELEGWEP. The publication suggests the use of full length survivin as an anti-cancer vaccine.

U.S. Pat. No. 7,579,436 discloses the use of various peptides, including FKEV, for sulfur and ammonia detection, using a sensory device coated with the peptides. U.S. Pat. No. 7,338,929 discloses immunogenic peptides derived from human IL-13 receptor alpha 2 (IL-13Rα2), inter alia SLDHFKECTV, HFKECTVEY, FKECTVEYEL and DHFKECTV, and a method for immunizing against IL-13Rα2-expressing cancer. U.S. Pat. App. Pub. No. 2012/0021970 discloses the use of the peptide YRFKEHWR for ameliorating mitochondria permeability. Additional polypeptides containing the amino acids FKE are described in WO 2009/027768, EP 0852234, U.S. Pat. No. 8,148,322, U.S. Pat. No. 6,165,730, WO 1999/057144, WO 1995/029938, U.S. Pat. No. 6,303,339, U.S. Pat. No. 5,856,444, U.S. Pat. No. 5,840,513, U.S. Pat. No. 6,664,230 and WO 2012/174117, incorporated herein by reference.

The amino acid sequence of murine lactoferrin comprises the sequence YKE. Certain polypeptides comprising YKE are further described, e.g. by EP 0445801, disclosing the hepatitis C virus epitope RRYKEKEK; U.S. Pat. No. 6,531,130 disclosing ordered peptides comprising a repeated (EYYK)$_{2-6}$ motif, useful as myelin basic protein agonists for treating or preventing demyelinating autoimmune diseases; WO 95/16462, disclosing EYKEYAEYAEYAEYA as a T cell receptor alpha antigen; U.S. Pat. No. 7,635,480, disclosing KAKPVQKLDDDDDGDDTTYKEERHNK and homologs thereof exhibiting at least 80% similarity useful in preventing, diagnosing and treating leptospirosis; and in WO 03/103572, U.S. Pat. No. 6,660,842 and U.S. Pat. No. 6,607,727, incorporated herein by reference.

None of the art discloses or suggests that an isolated FKE sequence or motif may exhibit an inflammation inhibiting activity. There remains an unmet medical need for providing therapeutic modalities for the treatment of inflammatory and fibrotic diseases.

SUMMARY OF THE INVENTION

The present invention is directed to synthetic anti-inflammatory peptides and use thereof in the treatment and prevention of inflammatory and fibrotic conditions.

The invention is based, in part, on the surprising discovery, that synthetic peptides comprising or consisting of the amino acid sequence Phe-Lys-Glu (FKE) are potent anti-inflammatory and anti-fibrotic agents. Under inflammatory conditions, these peptides were found to induce secretion of the anti-inflammatory and anti-fibrotic cytokine interleukin-10 (IL-10) from lipopolysaccharide (LPS)-activated human macrophages. In comparison, a peptide synthesized with replacement of only one amino acid, having the amino acid sequence FKD, was not effective in inducing IL-10 secretion under inflammatory conditions. In addition, the secretion of pro-inflammatory cytokines such as IL-6 or pro-fibrotic cytokines such as Transforming growth factor beta (TGF-β) was unexpectedly inhibited upon incubation with peptides comprising the sequences FKE or YKE (Tyr-Lys-Glu) at advantageously low concentrations, compared to their secretion in the presence of FKD. Notably, the reverse peptide EKF (Glu-Lys-Phe) did not reproduce these effects.

Accordingly, the present invention discloses new and surprising activities retained within the aforementioned amino acid motifs, thus facilitating new therapeutic methods in inhibiting inflammation and treating or preventing chronic and pathological inflammatory conditions. In particular, the invention provides methods for inhibiting fibrosis associated with inappropriate or excessive inflammation, and other reactions that are ameliorated by IL-10. Further provided herein are novel synthetic anti-inflammatory peptides, useful in the methods of the invention.

Thus, the invention is directed in various embodiments to methods for inhibiting inflammation and/or inflammation-induced fibrosis, for treating or preventing inflammatory and/or fibrotic diseases and for inhibiting scar formation and fibrotic scarring. In certain other embodiments, the invention provides methods for inducing or enhancing the secretion of anti-inflammatory and anti-fibrotic cytokines such as IL-10 and/or for reducing the secretion of the pro-fibrotic cytokine TGF-β, and for treating and alleviating IL-10 dependent conditions. The methods of the invention are affected in some embodiments by administration of isolated peptides having the amino acid sequence FKE and/or YKE, or synthetic peptides derived therefrom, as detailed herein.

Accordingly, a first aspect of the invention is directed to a pharmaceutical composition for use in treating or inhibiting inflammation in a subject in need thereof, comprising a synthetic, recombinant or isolated peptide having the amino acid sequence FKE (SEQ ID NO: 1), or a nucleic acid construct encoding same.

In one embodiment, said subject is identified as being afflicted with a disorder associated with an inappropriate or detrimental inflammatory response. According to some embodiments, the disorder is associated with fibrosis, or is an autoimmune disease or another chronic inflammatory disease.

According to certain embodiments, the subject may be afflicted with a chronic inflammatory disease, e.g. an autoimmune disease. According to other particular embodiments, the disease may be selected from the group consisting of peritonitis, mastitis, multiple sclerosis, autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis), autoimmune hepatitis and rheumatoid arthritis.

According to various other embodiments, the subject may be afflicted with a disease or disorder associated with fibrosis. For example, said disorder may be associated with fibrosis in the skin, in the lung, in the liver, in the kidney, of the central nervous system, in bone or bone marrow, in the cardiovascular system, in an endocrine organ or in the gastro-intestinal system. In another embodiment, the composition is used for inhibiting inflammation-induced fibrosis in said subject. According to other particular embodiments, the fibrosis may be associated with a fibrotic disease selected from the group consisting of cirrhosis of the liver, constrictive pericarditis, Dupuytren's disease of the hand, plantar fibrosis of the foot, chronic obstructive pulmonary disease (COPD), emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, chronic granulomatous disease (CGD), chronic diabetic wounds and fibrosis resulting after surgery. In another embodiment, said disorder is IL-10-dependent, namely is inhibited, ameliorated or alleviated by IL-10. In another embodiment, said disorder is associated with increased TGF-β levels and is inhibited or alleviated by increased IL-10 levels. In yet another embodiment, the composition is used for inhibiting scar formation in said subject.

In another embodiment said peptide is 3-20 amino acids (aa) in length. In another embodiment, said peptide contains a plurality of FKE sequences. In a particular embodiment, said peptide contains 2-5 repeated FKE sequences. The FKE sequences, particularly in peptides containing a plurality of repeated FKE sequences, may optionally be flanked by one or more linker sequences. The linker sequences may be of 1-7 aa, and preferably contain the amino acids alanine (A)

and/or glycine (G). In a particular embodiment said linker sequences consist of the amino acids alanine and/or glycine.

Thus, in another embodiment, said FKE sequences are flanked by linker sequences of 1-7 amino acids. According to particular embodiments the FKE sequences are flanked by linker sequences of 1-7 amino acids, wherein said linker sequences may contain the amino acids alanine and/or glycine, or may consist of the amino acids alanine and/or glycine. For example a peptide useful in the methods of the invention may contain 3 repeated FKE sequences each flanked by oligo-alanine, oligo-glycine or alanine-glycine oligomer linker sequences.

In another embodiment said peptide or composition may further comprise one or more YKE (SEQ ID NO: 2) sequences. In another embodiment said peptide or composition does not contain an FKD (SEQ ID NO: 3) sequence. According to certain other embodiments, said peptide may further contain flanking sequences from a mammalian lactoferrin molecule, e.g. bovine or murine lactoferrin. For example, the peptide FKECH (SEQ ID NO: 4) may be used for certain indications. In other embodiments the invention advantageously relates to synthetic peptides lacking the flanking lactoferrin sequences.

According to exemplary embodiments, said peptide is SEQ ID NO: 1. In other embodiments, said peptide may be chemically derivatized at the N- and/or C-terminus.

The invention relates in some embodiments to the treatment of a mammalian subject, e.g. a human or bovine subject. The peptide or composition may be administered to said subject by a variety of administration routes, as known in the art. According to certain embodiments, a topical administration route is envisaged, e.g. in the treatment or prevention of skin fibrosis and scarring. In other specific embodiments, administration by inhalation may be implemented, e.g. for inhibiting lung fibrosis and treating related conditions such as COPD, emphysema, idiopathic pulmonary fibrosis, acute lung injury and cystic fibrosis. In another embodiment said peptide is not administered in a vaccination protocol or formulation. In another embodiment, said peptide is formulated for topical administration.

According to other aspects, the invention provides novel peptides having anti-inflammatory and anti fibrotic properties. Thus, in another aspect, there is provided a synthetic, recombinant or isolated peptide of 3-20 amino acids in length having the amino acid sequence FKE, as set forth in any one of Formulae Ia and Ib as defined herein.

The peptides of the invention include in some embodiments a peptide of Formula Ia (SEQ ID NO: 9):

wherein:
- $X^1$ is an amino acid, a peptide of 2 to 7 amino acids other than YR and LDH, a chemical derivatizing group or is absent;
- $S^1$ is an amino acid other than K and R, a spacer of 2 to 7 amino acids comprising a plurality of A and/or G residues, or is absent;
- $S^2$ is an amino acid other than V, K and R, a spacer of 2 to 7 amino acids comprising a plurality of A and/or G residues, or is absent;
- $X^2$ is an amino acid, a peptide of 2 to 7 amino acids, a chemical derivatizing group or is absent; wherein when $S^2$ is absent, $X^2$ is not HWR, LEG, LEGWEP, CTV, CTVEY, CTVEYEL, CHL, CHLA or HLA.

The peptides of the invention include in other embodiments a peptide of Formula Ib (SEQ ID NO: 10):

wherein:
- n is an integer of 2-5;
- $X^1$ is an amino acid, a peptide of 2 to 7 amino acids, a chemical derivatizing group or is absent;
- $S^1$ is an amino acid, a spacer of 2 to 7 amino acids comprising a plurality of A and/or G residues, or is absent;
- $S^2$ is an amino acid, a spacer of 2 to 7 amino acids comprising a plurality of A and/or G residues, or is absent;
- $X^2$ is an amino acid, a peptide of 2 to 7 amino acids, a chemical derivatizing group or is absent.

In some embodiments, $S^1$ and/or $S^2$ as defined in Formulae Ia and Ib may individually be A, G, or spacer peptides consisting of A and/or G residues. In another embodiment the peptide is 3-10 amino acids in length. An exemplary peptide of the formula Ia is SEQ ID NO: 1, or peptides of SEQ ID NO: 1 which are chemically derivatized at the N- and/or C-terminus. In another embodiment the peptide comprises one or more YKE sequences. In another embodiment, the peptide induces IL-10 secretion from human macrophages.

In another embodiment, the invention relates to a peptide according to Formulae Ia and Ib, in which $X^1$ is not RGD, K, R, Q, Y, SQI, IN, H, DH, SLDH, AT or VDA. In another embodiment, $X^1$ does not contain RGD, K, R, Q, Y, SQI, IN, H, DH, SLDH, AT or VDA. In another embodiment, $S^1$ is not K, R Q, Y, S or T. In another embodiment $S^2$ is not V, K, R, Q, H, I, or L. In another embodiment $X^2$ is not HWR, LEG, LEGWEP, CTV, CTVEY, CTVEYEL, RGD, K, DI, KDI, ST, VT, Y, LA, CHL, CHLA or HLA. In another embodiment $X^2$ does not contain HWR, LEG, LEGWEP, CTV, CTVEY, CTVEYEL, RGD, K, DI, KDI, ST, VT, Y, LA, CHL, CHLA or HLA.

In another embodiment, there is provided a pharmaceutical composition containing an effective amount of a peptide according to any one of Formulae Ia and Ib, and one or more pharmaceutically accepted carriers, excipients or diluents.

In another embodiment, there is provided a method for inducing or enhancing IL-10 secretion in a subject in need thereof, comprising administering to the subject the peptide according to any one of Formulae Ia and Ib, thereby inducing or enhancing IL-10 secretion in said subject.

In another embodiment, the invention provides a method for treating an inflammatory disease in a subject in need thereof, comprising identifying the subject as suffering from the disease, and administering to said subject the peptide according to any one of Formulae Ia and Ib, thereby treating said inflammatory disease in said subject. In another embodiment the disease is selected from the group consisting of peritonitis, mastitis, multiple sclerosis, autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis), autoimmune hepatitis and rheumatoid arthritis.

In another embodiment, the invention provides a method for inhibiting inflammation-induced fibrosis in a subject in need thereof, comprising identifying the subject as suffering from or at risk of developing inflammation-induced fibrosis, and administering to said subject the peptide according to any one of Formulae Ia and Ib, thereby inhibiting said inflammation-induced fibrosis in said subject.

In another embodiment, the invention provides a method for treating or preventing a fibrotic disease in a subject in need thereof, comprising identifying the subject as suffering from or at risk of developing the fibrotic disease, and administering to said subject the peptide according to any one of Formulae Ia and Ib, thereby treating or preventing said fibrotic disease in said subject. In another embodiment said disease is associated with fibrosis in the skin, in the lung, in the liver, in the kidney, of the central nervous system, in bone or bone marrow, in the cardiovascular system, in an endocrine organ or in the gastro-intestinal system. In another embodiment said disease is a fibrotic disease selected from the group consisting of cirrhosis of the liver, constrictive pericarditis, Dupuytren's disease of the hand, plantar fibrosis of the foot, chronic obstructive pulmonary disease (COPD), emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, chronic granulomatous disease (CGD), chronic diabetic wounds and fibrosis resulting after surgery.

In another embodiment, the invention provides a method for inhibiting scar formation in a subject in need thereof, comprising administering to said subject the peptide according to any one of Formulae Ia and Ib, thereby inhibiting scar formation in said subject.

In another embodiment the invention relates to a nucleic acid construct encoding a peptide according to any one of Formulae Ia and Ib.

In another aspect there is provided a synthetic, recombinant or isolated peptide of 3-20 amino acids in length, having the amino acid sequence YKE, as set forth in any one of Formulae IIa and IIb as defined herein.

The peptides of the invention include in some embodiments a peptide of Formula IIa (SEQ ID NO: 11):

$$X^1-(S^1)(YKE)(S^2)-X^2 \quad \text{(IIa)}$$

wherein:
$X^1$ is an amino acid, a peptide of 2-7 amino acids other than RR, MDIDP, and KKNWIQ, a chemical derivatizing group or is absent;
$S^1$ is an amino acid, a spacer of 2-7 amino acids comprising a plurality of A and/or G residues, or is absent; wherein when $X^1$ is absent and $S^1$ is an amino acid, $S^1$ is not Y or E;
$S^2$ is an amino acid, a spacer of 2-7 amino acids comprising a plurality of A and/or G residues, or is absent; wherein $X^2$ is absent and $S^2$ is an amino acid, $S^2$ is not Y;
$X^2$ is an amino acid, a peptide of 2 to 7 amino acids, a chemical derivatizing group or is absent; wherein when $S^2$ is absent, $X^2$ is not KEK.

The peptides of the invention include in other embodiments a peptide of Formula IIb (SEQ ID NO: 12):

$$X^1-[(S^1)(YKE)(S^2)]_n-X^2 \quad \text{(IIb)}$$

wherein:
n is an integer of 2-5;
$X^1$ is an amino acid, a peptide of 2-7 amino acids, a chemical derivatizing group or is absent;
$S^1$ is an amino acid, a spacer of 2-7 amino acids comprising a plurality of A and/or G residues, or is absent;
$S^2$ is an amino acid, a spacer of 2-7 amino acids comprising a plurality of A and/or G residues, or is absent;
$X^2$ is an amino acid, a peptide of up to 7 amino acids, a chemical derivatizing group or is absent.

In another embodiment $X^2$ is not Y, ERHNK or KEK. In another embodiment $S^1$ is not Y or E. For example, a peptide according to Formula IIa may be a peptide of SEQ ID NO: 2, or a peptide of SEQ ID NO: 2 which is chemically derivatized at the N- and/or C-terminus.

In another embodiment there is provided a pharmaceutical composition containing an effective amount of a peptide according to any one of Formulae IIa and IIb and one or more pharmaceutically accepted carriers, excipients or diluents.

In another embodiment, the invention provides a method for treating an inflammatory disease in a subject in need thereof, comprising identifying the subject as suffering from the disease, and administering to said subject the peptide according to any one of Formulae IIa and IIb thereby treating said inflammatory disease in said subject. In another embodiment the disease is selected from the group consisting of peritonitis, mastitis, autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis), autoimmune hepatitis and rheumatoid arthritis.

In another embodiment the invention relates to a nucleic acid construct encoding a peptide according to any one of Formulae IIa and IIb.

Other objects, features and advantages of the present invention will become clear from the following description and drawings.

DETAILED DESCRIPTION OF THE INVENTION

Figure 1A:
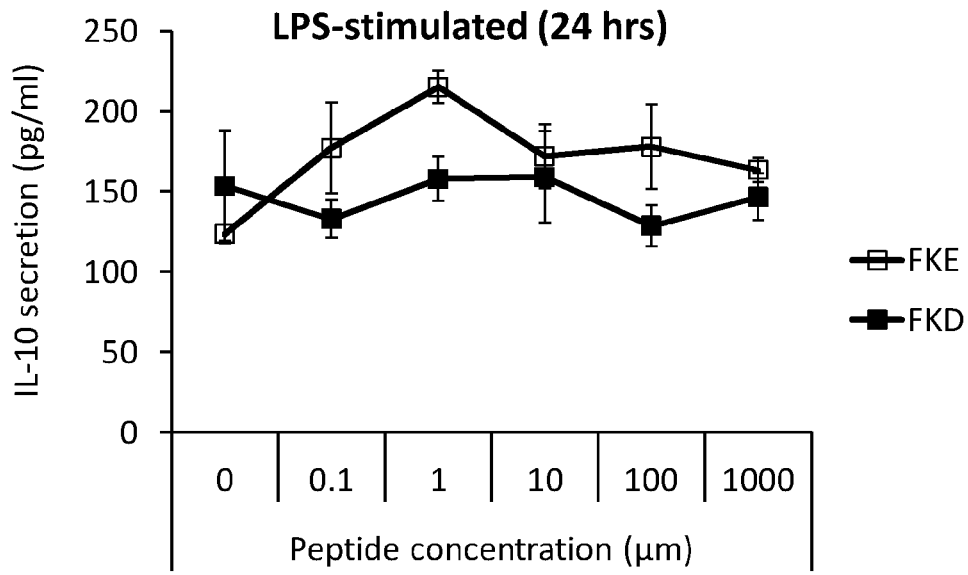
FIG. 1. Human macrophages were treated with the indicated concentrations of FKE (open squares) or FKD (closed squares) peptides for 24 hrs. Then, the cells were treated with LPS and incubation was continued for additional 24 hrs. Next, culture supernatants were collected and their content of IL-10, TGF-β and IL-6, (FIGS. 1A, 1B and 1C, respectively) was determined by standard ELISA.

The present invention is directed to synthetic anti-inflammatory peptides and use thereof in the treatment and prevention of inflammatory and fibrotic conditions. Specifically, the invention relates in some embodiments to short isolated peptides having the amino acid sequence FKE or YKE, or a plurality of these sequences, which may be flanked by A/G linkers. The invention further relates in some embodiments to methods for inhibiting scar formation and for treating and alleviating IL-10 dependent conditions.

The invention is based, in part, on the surprising discovery, that synthetic peptides comprising or consisting of the amino acid sequence FKE are capable of inducing the secretion of the anti-inflammatory and anti-fibrotic cytokine IL-10 from LPS-activated human macrophages. In comparison, a peptide synthesized with replacement of only one amino acid, having the amino acid sequence FKD, was not effective in inducing IL-10 secretion under inflammatory conditions. The FKD motif was hitherto reported to be associated with pro-inflammatory activity and induction of inflammatory cytokine and chemokine secretion, while the FKE motif was reported to be inactive (Komine et al. J Vet Med Sci. 2006 July; 68(7):715-23). In addition, the secretion of pro-inflammatory cytokines such as IL-6 or pro-fibrotic cytokines such as TGF-β was unexpectedly inhibited upon incubation with peptides comprising the sequences FKE or YKE at advantageously low concentrations. Notably, the reverse peptide EKF did not reproduce these effects.

Accordingly, a first aspect of the invention is directed to a method for treating or inhibiting inflammation in a subject in need thereof, comprising administering to the subject a synthetic, recombinant or isolated peptide having the amino acid sequence FKE (SEQ ID NO: 1), a peptide of the invention as described herein, or a nucleic acid construct encoding same, thereby inhibiting inflammation in said subject.

In another aspect, there is provided a method for inducing or enhancing IL-10 secretion in a subject in need thereof, comprising administering to the subject a synthetic, recombinant or isolated peptide having the amino acid sequence FKE, a peptide of the invention as described herein, or a nucleic acid construct encoding same, thereby inducing or enhancing IL-10 secretion in said subject. In another embodiment, the method induces or enhances IL-10 secretion from mononuclear cells. In another embodiment, the method induces or enhances IL-10 secretion from macrophages.

In another aspect, there is provided a method for treating an inflammatory disease in a subject in need thereof, comprising identifying the subject as suffering from the disease, and administering to said subject a synthetic, recombinant or isolated peptide having the amino acid sequence FKE (SEQ ID NO: 1), a peptide of the invention as described herein, or a nucleic acid construct encoding same, thereby treating said inflammatory disease in said subject.

In another aspect, the invention provides a method for inhibiting inflammation-induced fibrosis in a subject in need thereof, comprising identifying the subject as suffering from or at risk of developing inflammation-induced fibrosis, and administering to said subject a synthetic, recombinant or isolated peptide having the amino acid sequence FKE (SEQ ID NO: 1), a peptide of the invention as described herein, or a nucleic acid construct encoding same, thereby inhibiting said inflammation-induced fibrosis in said subject.

In another aspect, the invention provides a method for treating or preventing a fibrotic disease in a subject in need thereof, comprising identifying the subject as suffering from or at risk of developing the fibrotic disease, and administering to said subject a synthetic, recombinant or isolated peptide having the amino acid sequence FKE (SEQ ID NO: 1), a peptide of the invention as described herein, or a nucleic acid construct encoding same, thereby treating or preventing said fibrotic disease in said subject.

In another aspect, there is provided a method for inhibiting scar formation in a subject in need thereof, comprising administering to said subject a synthetic, recombinant or isolated peptide having the amino acid sequence FKE (SEQ ID NO: 1), a peptide of the invention as described herein or a nucleic acid construct encoding same, thereby inhibiting scar formation in said subject.

Another aspect of the invention is directed to a pharmaceutical composition for use in treating or inhibiting inflammation in a subject in need thereof, comprising a synthetic, recombinant or isolated peptide having the amino acid sequence FKE (SEQ ID NO: 1), a peptide of the invention as described herein, or a nucleic acid construct encoding same. In a particular embodiment, the composition comprises the peptide having the amino acid sequence FKE (SEQ ID NO: 1). In other particular embodiments, the composition comprises a peptide as set forth in any one of Formulae Ia, Ib, IIa and IIb as defined herein, wherein each possibility represents a separate embodiment of the invention.

Another aspect of the invention is directed to a pharmaceutical composition comprising a synthetic, recombinant or isolated peptide having the amino acid sequence FKE (SEQ ID NO: 1), a peptide of the invention as described herein, or a nucleic acid construct encoding same, for use in inducing or enhancing IL-10 secretion, in treating an inflammatory disease, in inhibiting inflammation-induced fibrosis, in treating or preventing a fibrotic disease, or in inhibiting scar formation in a subject in need thereof.

According to various other aspects, the invention provides synthetic, recombinant or isolated peptides of 3-20 amino acids in length as set forth in any one of Formulae Ia, Ib, IIa and IIb, wherein each possibility represents a separate embodiment of the invention.

Peptides

The peptides of the invention may be isolated or synthesized using any recombinant or synthetic method known in the art, including, but not limited to, solid phase (e.g. Boc or f-Moc chemistry) and solution phase synthesis methods. For example, the peptides can be synthesized by a solid phase peptide synthesis method of Merrifield (1963 J. Amer. Chem. Soc. 85:2149-2156). Alternatively, a peptide of the present invention can be synthesized using standard solution methods well known in the art (see, for example, Bodanszky, 1984 The Principles of Peptide Synthesis, Springer-Verlag, New York) or by any other method known in the art for peptide synthesis.

In alternate embodiments, the peptides may be produced by recombinant technology. Recombinant methods for designing, expressing and purifying proteins and peptides are known in the art (see, e.g. Sambrook et al., Molecular Cloning: A Laboratory Manual, Cold Springs Harbor Laboratory, New York, 2001). Nucleic acid molecules according to the invention may include DNA, RNA, or derivatives of either DNA or RNA. An isolated nucleic acid sequence encoding a peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention. A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Moreover, polynucleotides that include more or less nucleotides can result in the same or equivalent proteins. Thus, according to other embodiments, the invention provides nucleic acids encoding the peptides of the invention, as well as recombinant constructs, expression vectors and pharmaceutical compositions thereof as known in the art (see, e.g. Sambrook et al., 2001).

In the methods of the invention, the term "peptide" relates to a sequence of 3-50 preferably 3-40 contiguous amino acids, linked by peptide bonds. The peptide may include both "L" and "D" amino acids as well as non-natural and chemically derivatized amino acids known in the art. Preferably, the peptides of the invention are 3-30 amino acids (aa) in length, more preferably 3-20 aa or 3-19 aa in length. According to particular embodiments, short peptides of 19, 18, 17, 16, 15, 14, 13, 12, 11, 10, 9, 8, 7, 6, 5, 4, or 3 aa in length are contemplated.

As used herein, the term "isolated peptide" refers to either a synthetic peptide or a peptide which has been "altered by the hand of man" and separated from the co-existing materials of its natural state. An isolated peptide has been synthetically produced or changed or removed from its original environment and typically both.

Whenever peptides are mentioned in the invention, also salts and functional derivatives thereof are contemplated, as long as they retain the biologic functions of the peptide, as detailed herein. Thus, the present invention encompasses peptides containing non-natural amino acid derivatives or non-protein side chains. The peptides of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid. Generally, any pharmaceutically acceptable salt of the peptide of the invention may be used, as long as the biological activities of the peptide are maintained.

The amino acid residues described herein are preferred to be in the "L" isomeric form. However, residues in the "D" isomeric form can be substituted for L-amino acid residues, as long as the peptide substantially retains the desired functional property. For example, "retro-inverso" peptides (peptidomimetics), i.e. peptides consisting of D-amino acids in the reversed sequence order, share a similar arrangement of side-chains as the native "all L" peptides, while their carboxyl and amino groups point in opposing directions. For small peptides that do not depend on a secondary structure for binding, such as peptides of the invention, an L-peptide and its D-retro-inverso-peptide are likely to have a similar binding affinity with a target L-protein. Thus, for example, when embodiments of the invention recite a sequence of the amino acid sequence FKE or YKE, their respective retro-inverso peptides are further included.

The N' and C' of the peptides may optionally be derivatized by stabilizing chemical groups as known in the art, which do not substantially affect the structure or conformation of the peptide, such as by amidation, acetylation, conjugation of fatty acids and the like. A peptide "chemically derivatized at the N- and/or C-terminus" as used herein represents a peptide to which such chemical groups have been conjugated. In other embodiments, the peptide has free (non-derivatized) N' and C' termini. In certain embodiments the peptide is linear or substantially linear. Yet in other embodiments cyclic peptides are contemplated, in which the amino and carboxy termini are themselves linked together with a covalent bond, including but not limited to a peptide bond, forming a continuous (e.g. circular) chain.

Thus, for example, the "chemical derivatizing group(s)" represented in Formulae Ia, Ib, IIa and IIb herein in positions $X^1$ and $X^2$ are chemical groups that are routinely used in the art of peptide chemistry to confer biochemical stability or resistance to digestion by exopeptidases. Exemplary N-terminal derivatizing groups include, for example, $C_{1-5}$ alkanoyl groups such as acetyl; other exemplary blocking groups include, without limitation, t-butyloxycarbonyl, methyl, succinyl, methoxysuccinyl, suberyl, adipyl azelayl, dansyl, benzyloxycarbonyl, fluorenylmethoxycarbonyl, methoxyaselayl, methoxyadipyl, methoxysuberyl, and 2,3-dinitrophenyl groups. Also suitable as N-terminal protecting groups are amino acid analogs lacking the amino function. Exemplary C-terminal derivatizing groups include groups which form ketones or amides at the carbon atom of the C-terminal carboxyl, or groups which form esters at the oxygen atom of the carboxyl. Ketone and ester-forming groups include alkyl groups, e.g., methyl, ethyl, and propyl groups, while amide-forming groups include amino functions such as primary amine, or alkylamino functions, e.g., mono-$C_{1-5}$ alkylamino and di-$C_{1-5}$ alkylamino groups such as methylamino, ethylamino, dimethylamino, diethylamino, methylethylamino and the like. Amino acid analogs are also suitable for protecting the C-terminal end of the present compounds, for example, decarboxylated amino acid analogues such as agmatine.

In some embodiments the peptide contains a plurality of FKE sequences, e.g. 2-5 repeated FKE sequences. The FKE sequences, particularly in peptides containing a plurality of repeated FKE sequences, may optionally be flanked by one or more linker sequences. The linker sequences may be of 1-7 aa, and preferably contain the amino acids alanine (A) and/or glycine (G). For example a peptide useful in the methods of the invention may contain 3 repeated FKE sequences each flanked by oligo-alanine, oligo-glycine or alanine-glycine oligomer linkers. In a particular embodiment said linker sequences consist of the amino acids alanine and/or glycine.

In some embodiments, said peptide further comprises one or more YKE (SEQ ID NO: 2) sequences. In other embodiments, said peptide does not contain an FKD (SEQ ID NO: 3) sequence. According to certain other embodiments, said peptide may further contain flanking sequences from a mammalian lactoferrin molecule, e.g. bovine or murine lactoferrin. For example, the peptide FKECH (SEQ ID NO: 4) may be used for certain indications. In other embodiments the invention advantageously relates to synthetic peptides lacking the flanking lactoferrin sequences. In some preferred embodiments said peptide is SEQ ID NO: 1, optionally chemically derivatized at the N- and/or C-terminus.

According to other aspects, the invention provides novel peptides having anti-inflammatory and anti fibrotic properties. Thus, in another aspect there is provided a synthetic, recombinant or otherwise isolated peptide of 3-20 amino acids in length, of the following Formula I:

$$X^1 - [(S^1)(FKE)(S^2)]_n - X^2 \qquad (I)$$

wherein:

n is an integer of 1 to 5;

$X^1$ is an amino acid, a peptide of 2 to 7 amino acids other than YR and LDH, a chemical derivatizing group or is absent;

$S^1$ is an amino acid, a spacer of 2 to 7 amino acids comprising a plurality of A and/or G residues, or may be absent; wherein when n=1, $X^1$ is absent and $S^1$ is an amino acid, $S^1$ is not K or R;

$S^2$ is an amino acid, a spacer of 2 to 7 amino acids comprising a plurality of A and/or G residues, or may be absent; wherein when n=1, $X^2$ is absent and $S^2$ is an amino acid, $S^2$ is not V, K or R;

$X_2$ is an amino acid, a peptide of 2 to 7 amino acids, a chemical derivatizing group or is absent; wherein when n=1 and $S^2$ is absent, $X^2$ is not HWR, LEG, LEGWEP (SEQ ID NO: 13), CTV, CTVEY (SEQ ID NO: 14), CTVEYEL (SEQ ID NO: 15), CHL, CHLA SEQ ID NO: 16) or HLA.

In a particular embodiment, the peptide according to Formula I is represented by Formula Ia, as defined herein (SEQ ID NO: 9). In another particular embodiment, the peptide according to Formula I is represented by Formula Ib, as defined herein (SEQ ID NO: 10).

In another embodiment, the invention relates to a peptide according to Formula I (e.g. Ia and Ib), in which $X^1$ is not RGD, K, R, Q, Y, SQI, IN, H, DH, SLDH (SEQ ID NO: 17), AT or VDA. In another embodiment, $X^1$ does not contain RGD, K, R, Q, Y, SQI, IN, H, DH, SLDH, AT or VDA. In another embodiment $X^1$ is absent.

In another embodiment, $S^1$ is not K, R, Q, Y, S or T. In another embodiment, $S^2$ is not V, K, R, Q, H, I, or L. In a preferred embodiment $S^1$ and/or $S^2$ are individually A, G, or spacer peptides consisting of A and/or G residues. The spacers may be 1, 2, 3, 4, 5, 6, or 7 amino acids in length. For example, without limitation, $S^1$ and/or $S^2$ may be oligo-A pentapeptides or oligo-G pentapeptides. In another embodiment $S^1$ is absent. In another embodiment $S^2$ is absent. In another embodiment $S^1$ and $S^2$ are absent.

In another embodiment $X^2$ is not HWR, LEG, LEGWEP, CTV, CTVEY, CTVEYEL, RGD, K, DI, KDI, ST, VT, Y, LA, CHL, CHLA or HLA. In another embodiment $X^2$ does not contain HWR, LEG, LEGWEP, CTV, CTVEY, CTVEYEL, RGD, K, DI, KDI, ST, VT, Y, LA, CHL, CHLA or HLA. In another embodiment $X^2$ is absent. In another embodiment, $X^1$ and $X^2$ are absent.

In another embodiment said peptide is 3-10 amino acids in length. In a particular embodiment said peptide is SEQ ID NO: 1. In another particular embodiment said peptide is SEQ ID NO: 1 that is chemically derivatized at the N- and C-termini. In another particular embodiment said peptide is SEQ ID NO: 1 that is chemically derivatized at the N-terminus. In another particular embodiment said peptide is SEQ ID NO: 1 that is acetylated at the N-terminus. In another particular embodiment said peptide is SEQ ID NO: 1 that is chemically derivatized at the C-terminus. In another particular embodiment said peptide is SEQ ID NO: 1 that is amidated at the C-terminus. In another embodiment the peptide is SEQ ID NO: 1 that is not chemically derivatized at the N- and C-termini. In another embodiment, said peptide is SEQ ID NO: 4, or a peptide of SEQ ID NO: 4 which is chemically derivatized at the N- and/or C-terminus (e.g. by acetylation or amidation), wherein each possibility represents a separate embodiment of the invention.

In another embodiment said peptide comprises one or more YKE sequences. For example, in various embodiments, $X^1$, $X^2$, $S^1$ and/or $S^2$ may contain a YKE sequence, wherein each possibility represents a separate embodiment of the invention.

In another embodiment said peptide does not comprise an FKD sequence. It should be understood, that the synthetic peptides as defined by Formula I herein are disclosed with the proviso that said peptide is not FKECHLA (SEQ ID NO: 21) or other isolated or synthetic peptides known in the art such as those described hereinabove.

In another embodiment, n is an integer of 2-5. In various specific embodiments, n may be 1, 2, 3, 4 or 5, wherein each possibility represents a separate embodiment of the invention.

For example, the following synthetic peptides are contemplated:

```
                                         (SEQ ID NO: 5)
FKEAAAAAFKEAAAAAFKEAAAAAFKEAAAAAFKE;

(SEQ ID NO: 6)
FKEGGGGGFKEGGGGGFKEGGGGGFKEGGGGGFKE;

(SEQ ID NO: 7)
Acetyl-FKE-amide;
and (SEQ ID NO: 8)
Acetyl-AAAAAFKEAAAAAFKEAAAAAFKEAAAAA-amide.
```

In another aspect, there is provided a synthetic, recombinant or otherwise isolated peptide of 3-20 amino acids in length, of the following Formula II:

$$X^1-[(S^1)(YKE)(S^2)]_n-X^2 \quad \text{(II)}$$

wherein:

n is an integer of 1-5;

$X^1$ is an amino acid, a peptide of 2-7 amino acids other than RR, MDIDP (SEQ ID NO: 18), and KKNWIQ (SEQ ID NO: 19), a chemical derivatizing group or is absent;

$S^1$ is an amino acid, a spacer of 2-7 amino acids comprising a plurality of A and/or G residues, or may be absent; wherein when n=1, $X^1$ is absent and $S^1$ is an amino acid, $S^1$ is not Y or E;

$S^2$ is an amino acid, a spacer of 2-7 amino acids comprising a plurality of A and/or G residues, or may be absent; wherein when n=1, $X^2$ is absent and $S^2$ is an amino acid, $S^2$ is not Y;

$X^2$ is an amino acid, a peptide of up to 7 amino acids, a chemical derivatizing group or is absent; wherein when n=1 and $S^2$ is absent, $X^2$ is not KEK.

In a particular embodiment, the peptide according to Formula II is represented by Formula IIa, as defined herein (SEQ ID NO: 11). In another particular embodiment, the peptide according to Formula II is represented by Formula IIb, as defined herein (SEQ ID NO: 12).

In another embodiment $X^2$ in Formula II (e.g. IIa or IIb) is not Y, ERHNK (SEQ ID NO: 20) or KEK. In another embodiment $X^1$ is absent.

In another embodiment $S^1$ is not Y or E. In various embodiments the spacers may be 1, 2, 3, 4, 5, 6, or 7 amino acids in length. For example, without limitation, $S^1$ and/or $S^2$ may be oligo-A pentapeptides or oligo-G pentapeptides. In another embodiment $S^1$ is absent. In another embodiment $S^2$ is absent. In another embodiment $S^1$ and $S^2$ are absent.

In another embodiment $X^2$ is absent. In another embodiment, $X^1$ and $X^2$ are absent.

In a particular embodiment, said peptide is SEQ ID NO: 2, or a peptide of SEQ ID NO: 2 which is chemically derivatized at the N- and/or C-terminus. In another particular embodiment said peptide is SEQ ID NO: 2 that is chemically derivatized at the N- and C-termini. In another particular embodiment said peptide is SEQ ID NO: 2 that is chemically derivatized at the N-terminus. In another particular embodiment said peptide is SEQ ID NO: 2 that is acetylated at the N-terminus. In another particular embodiment said peptide is SEQ ID NO: 2 that is chemically derivatized at the C-terminus. In another particular embodiment said peptide is SEQ ID NO: 2 that is amidated at the C-terminus. In another embodiment the peptide is SEQ ID NO: 2 that is not chemically derivatized at the N- and C-termini.

Pharmaceutical Compositions

In another aspect, the invention provides a pharmaceutical composition containing an effective amount of a peptide of the invention and one or more pharmaceutically accepted carriers, excipients or diluents.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable", "physiologically suitable" and "pharmaceutically acceptable", which may be used interchangeably, when used to describe carriers, excipients or diluents, refer to such materials that do not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference (Remington: The Science and Practice of Pharmacy, Gennaro, A., Lippincott, Williams & Wilkins, Philidelphia, Pa., $20^{th}$ ed, 2000).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are suitable for administration systemically or in a local manner, for example, via injection of the pharmaceutical composition directly into a tissue region of a patient. In a particular embodiment, the peptides are administered by injection, e.g. subcutaneously.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein.

The pharmaceutical compositions of the invention are also useful for topical and intralesional application. As used herein, the term "topical" means pertaining to a particular surface area and the topical agent applied to a certain area of said surface will affect only the area to which it is applied. The present invention provides, in some embodiments, topical compositions comprising the peptides of the invention as active ingredients. In some embodiments, the invention provides compositions consisting essentially of said peptides, e.g. the peptides of Formula I as described herein.

Topical pharmaceutical compositions may comprise, without limitation, non-washable (water-in-oil) creams or washable (oil-in-water) creams, ointments, lotions, gels, suspensions, aqueous or cosolvent solutions, salves, emulsions, wound dressings, coated bandages or other polymer coverings, sprays, aerosols, liposomes and any other pharmaceutically acceptable carrier suitable for administration of the drug topically. In certain particular embodiments, wound dressing formulations are provided.

As is well known in the art the physico-chemical characteristics of the carrier may be manipulated by addition a variety of excipients, including but not limited to thickeners, gelling agents, wetting agents, flocculating agents, suspending agents and the like. These optional excipients will determine the physical characteristics of the resultant formulations such that the application may be more pleasant or convenient. It will be recognized by the skilled artisan that the excipients selected, should preferably enhance and in any case must not interfere with the storage stability of the formulations.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

For example, a cream formulation may comprise in addition to the active compound: (a) a hydrophobic component; (b) a hydrophilic aqueous component; and (c) at least one emulsifying agent. The hydrophobic component of the cream is exemplified by the group consisting of mineral oil, yellow soft paraffin (Vaseline), white soft paraffin (Vaseline), paraffin (hard paraffin), paraffin oil heavy, hydrous wool fat (hydrous lanolin), wool fat (lanolin), wool alcohol (lanolin alcohol), petrolatum and lanolin alcohols, beeswax, cetyl alcohol, almond oil, arachis oil, castor oil, hydrogenated castor oil wax, cottonseed oil, ethyl oleate, olive oil, sesame oil, and mixtures thereof. The hydrophilic aqueous component of the cream is exemplified by water alone, propylene glycol or alternatively any pharmaceutically acceptable buffer or solution. Emulsifying agents are added to the cream in order to stabilize the cream and to prevent the coalescence of the droplets. The emulsifying agent reduces the surface tension and forms a stable, coherent interfacial film. A suitable emulsifying agent may be exemplified by but not limited to the group consisting of cholesterol, cetostearyl alcohol, wool fat (lanolin), wool alcohol (lanolin alcohol), hydrous wool fat (hydrous lanolin), and mixtures thereof.

A topical suspension, for example, may comprise in addition to the active compound: (a) an aqueous medium; and (b) suspending agents or thickeners. Optionally additional excipients are added. Suitable suspending agent or thickeners may be exemplified by but not limited to the group consisting of cellulose derivatives like methylcellulose, hydroxyethylcellulose and hydroxypropyl cellulose, alginic acid and its derivatives, xanthan gum, guar gum, gum arabic, tragacanth, gelatin, acacia, bentonite, starch, microcrystalline cellulose, povidone and mixture thereof. The aqueous suspensions may optionally contain additional excipients e.g. wetting agents, flocculating agents, thickeners, and the like. Suitable wetting agents are exemplified by but not limited to the group consisting of glycerol polyethylene glycol, polypropylene glycol and mixtures thereof, and surfactants. The concentration of the wetting agents in the suspension should be selected to achieve optimum dispersion of the pharmaceutical powders within the suspension with the lowest feasible concentration of the wetting agent. Suitable flocculating agents are exemplified by but not limited to the group consisting of electrolytes, surfactants, and polymers. The suspending agents, wetting agents and flocculating agents are provided in amounts that are effective to form a stable suspension of the pharmaceutically effective agent.

Topical gel formulation, for example, may comprise in addition to the active compound, at least one gelling agent and an acid compound. Suitable gelling agents may be exemplified by but not limited to the group consisting of hydrophilic polymers, natural and synthetic gums, crosslinked proteins and mixture thereof. The polymers may comprise for example hydroxyethylcellulose, hydroxyethyl methylcellulose, methyl cellulose, hydroxypropylcellulose, hydroxypropyl methylcellulose, carboxymethyl cellulose, and similar derivatives of amylose, dextran, chitosan, pullulan, and other polysaccharides; Crosslinked proteins such as albumin, gelatin and collagen; acrylic based polymer gels such as Carbopol, Eudragit and hydroxyethyl methacrylate based gel polymers, polyurethane based gels and mixtures thereof.

Topical pharmaceutical compositions of the present invention may additionally be formulated as a solution. Such a solution comprises, in addition to the active compound, at least one co-solvent exemplified but not limited to the group consisting of water, buffered solutions, organic solvents such as ethyl alcohol, isopropyl alcohol, propylene glycol, polyethylene glycol, glycerin, glycoforol, Cremophor, ethyl lactate, methyl lactate, N-methylpyrrolidone, ethoxylated tocopherol and mixtures thereof.

The composition of the invention may be used for transmucosal, e.g. transdermal delivery. The term "transdermal" delivery as used herein refers to the site of delivery of a pharmaceutical agent. Typically, the delivery is intended to the blood circulation. However, the delivery can include intra-epidermal or intradermal delivery, i.e., to the epidermis or to the dermal layers, respectively, beneath the stratum corneum. For transmucosal administration, penetrants appropriate to the barrier to be permeated are used in the formulation. Such penetrants are generally known in the art.

There are two prevalent types of transdermal patch designs, namely the reservoir type where the drug is contained within a reservoir having a basal surface that is permeable to the drug, and a matrix type, where the drug is dispersed in a polymer layer affixed to the skin Both types of designs also typically include a backing layer and an inner release liner layer that is removed prior to use. Preparation of such transdermal patches is within the ability of those of skill in the art; see, for example, U.S. Pat. Nos. 5,560,922, 4,559,222, 5,230,898 and 4,668,232 for examples of patches suitable for transdermal delivery of a therapeutic agent.

The peptides of the invention may also be formulated for administration by inhalation, e.g. in the form of an aerosol or a dry powder, and may conveniently employ the use of appropriate devices known in the art to facilitate delivery by inhalation (e.g. pulmonary delivery). For example, a pharmaceutical composition comprising a peptide of the invention and an aqueous solution may be delivered in the form of an aerosol spray from pressured container or dispenser which contains a suitable propellant, e.g., a gas such as carbon dioxide, or a nebulizer. Alternatively, a pharmaceutical composition comprising a peptide of the invention may be formulated in the form of a dry powder, which composition is administered using a dry powder inhaler. Other methods and devices known in the art for administration of a solution or powder by inhalation such as, for example, droplets, sprays, and nebulizers, can be useful. For example, for by-inhalation administration (i.e., delivery to the bronchopulmonary mucosa), suitable sprays and aerosols can be used, for example, with a nebulizer, such as those described in U.S. Pat. Nos. 4,624,251; 3,703,173; 3,561,444; and 4,635,627. The aerosol material is inhaled by the subject to be treated.

Pharmaceutical compositions suitable for use in the context of the present invention include compositions wherein the active ingredients are contained in an amount effective to achieve the intended purpose. Determination of a therapeutically effective amount is well within the capability of those skilled in the art. For example, without limitation, a concentration of 0.01-500, 1-250 or 10-100 µM may be suitable for use in a solution for injection or for topical, transmucosal, pulmonary or ex-vivo treatment in some embodiments, and a dosage of 0.05-50, 0.1-20, 0.05-10 or 0.5-2 mg/kg may in some embodiments be suitable for administration to a human subject.

According to some embodiments, the peptides of the invention are particularly advantageous at low doses, providing enhanced efficacy (e.g. enhanced IL-10 secretion) and improved safety. Thus, dosing schedules providing plasma concentrations of 1-50 µM may be suitable according to certain preferable embodiments. According to some embodiments, solutions for injection or compositions for topical, transmucosal or pulmonary application may advantageously be provided at peptide concentrations of 10-100 µM, e.g. 50 µM of a peptide of SEQ ID NO:1 or Formula I. According to other exemplary advantageous embodiments, administration by daily i.p. injection of 0.5-2 mg/KG of a peptide of the invention, e.g. of SEQ ID NO: 1 or Formula I, is envisaged. Extrapolation of suitable dosing schedules for other administration routes based on the doses and schedules disclosed herein is well within the ability of the skilled artisan.

Therapeutic Use

In some embodiments, the methods of the invention (e.g. the method of treating or inhibiting inflammation) comprise, prior to administering the treatment (e.g. peptide or composition of the invention), a step of identifying said subject as a subject afflicted with a disorder associated with an inappropriate or detrimental inflammatory response.

An inflammatory response may be detrimental in terms of magnitude or may be spatially or temporally inappropriate, thus contributing to the etiology or pathology of the disorder. An immune response may be evaluated by determining or quantifying various immune mediators such as antibodies or cytokines (e.g. IL-10), or by determining the state (phenotype) of immune cell mediators such as T cells, B cells, macrophages etc', using procedures well known in the art. Certain non-limitative methods for evaluating such immune mediators are described in the Examples below. Various disorders associated with such inappropriate or detrimental immune reactions have been identified, as detailed below.

In another embodiment, the disorder is associated with fibrosis. Thus, the methods may include a step of identifying said subject as a subject afflicted with, or predisposed to developing fibrosis. According to particular embodiments, said disorder may be associated with fibrosis in the skin, in the lung, in the liver, in the kidney, of the central nervous system, in bone or bone marrow, in the cardiovascular system, in an endocrine organ or in the gastro-intestinal system. For example, without limitation, said disorder may be a fibrotic disease selected from the group consisting of cirrhosis of the liver, constrictive pericarditis, Dupuytren's disease of the hand, plantar fibrosis of the foot, COPD, emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, chronic granulomatous disease (CGD) chronic diabetic wounds and fibrosis resulting after surgery. In any of the embodiments described above, the inflammatory or fibrotic disease can be chosen from pulmonary disease including pulmonary fibrosis and acute respiratory distress syndrome, liver disease including liver cirrhosis and kidney disease including renal interstitial fibrosis. Each possibility represents a separate embodiment of the invention. In a particular embodiment, the methods of the invention are used for inhibiting lung fibrosis, e.g. associated with lung fibrosis or other pulmonary diseases such as COPD, emphysema, idiopathic pulmonary fibrosis, acute lung injury and cystic fibrosis. In another particular embodiment the methods of the invention are used for inhibiting fibrotic disorders of the liver, including cirrhosis of the liver (advanced liver fibrosis) and fibrosis associated with autoimmune hepatitis. In yet another particular embodiment, the methods of the invention are used for inhibiting fibrosis in the skin and treating or preventing e.g. keloid, scleroderma, hypertrophic burn scars and chronic diabetic wounds.

In another embodiment, said disorder is a chronic inflammatory disease. A chronic inflammatory disease is characterized by a persistent inflammatory response with pathologic sequelae. This state is typically characterized by infiltration of mononuclear cells, proliferation of fibroblasts and small blood vessels, increased connective tissue, and tissue destruction. In a particular embodiment, said disorder is an autoimmune disease, including, without limitation, multiple sclerosis, autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis), autoimmune hepatitis and rheumatoid arthritis. Each possibility represents a separate embodiment of the invention. Autoimmune diseases involve the pathological or dysregulated activity of autoimmune T cells and/or antibodies, directed against self antigens.

Yet in other embodiments, the treatment of acute inflammatory diseases is contemplated. Acute inflammatory reactions are known to include changes in vascular permeability, edema and cellular infiltration, notably of granulocyte origin. In another embodiment the inflammatory disease is peritonitis i.e. inflammation of the peritoneal cavity. The most serious cause is perforation of the GI tract, which causes immediate chemical inflammation followed shortly by infection from intestinal organisms. Peritonitis can also result from any abdominal condition that causes marked inflammation (e.g., appendicitis, diverticulitis, strangulating intestinal obstruction, pancreatitis, pelvic inflammatory disease, mesenteric ischemia). In another embodiment the inflammatory disease is mastitis, i.e. inflammation of a mammary gland or an udder. Mastitis is most commonly caused by bacterial invasion and their toxins. Mastitis causes lactating women to experience pain when nursing the child, it damages mammary tissue, and the formation of scar tissue in the breast may cause disfigurement. In dairy cattle, mastitis is believed to be the most economically important disease.

In another embodiment, said disorder is IL-10-dependent, namely is inhibited, ameliorated or alleviated by IL-10. In another embodiment, said disorder is associated with increased TGF-β levels and is inhibited or alleviated by increased IL-10 levels. In another embodiment, said disorder is TGF-β dependent, namely is induced or enhanced by TGF-β, or is inhibited, ameliorated or alleviated by inhibiting or reducing TGF-β activity or secretion.

The term "Inflammation-induced fibrosis" relates to fibrosis developing during inflammatory diseases i.e. diseases related to acute or chronic inflammation (caused by tissue injury, pathogen infections or toxic agents) or as a consequence. Fibrosis is the formation of excess fibrous connective tissue during the reparative and reactive process of inflammation. In the context of the present invention, the term "fibrosis" will also be used with the same meaning as "inflammation-induced fibrosis".

As used herein, "preventing" a disease or condition relates to a process by which the symptoms of the disease or condition are obstructed or delayed. "Treating" a disease or condition relates to a process by which the symptoms of the disease or condition are alleviated or eliminated.

The methods of the invention relate in some embodiments to the treatment of a mammalian subject, e.g. a human or bovine subject. In the methods of the invention, the peptide may be administered to said subject by a variety of administration routes, as known in the art. According to certain embodiments, a topical administration route is envisaged, e.g. in the treatment or prevention of skin fibrosis and scarring. In other specific embodiments, administration by inhalation may be implemented, e.g. for inhibiting lung fibrosis and treating related conditions as described herein. In another embodiment said peptide is not administered in a vaccination protocol or formulation.

In the methods of the invention, administering refers to administration of the respective therapeutic agent (e.g. peptide of Formulae Ia-IIb) at a therapeutically effective dose as detailed herein, so as to exert the required (e.g. inflammation-inhibiting) activity. In some embodiments, ex vivo administration or treatment is contemplated. For example, cells of a subject collected e.g. from blood (e.g. leukocytes such as monocytes and macrophages, lymphocytes such as B cells or T cells) or from in situ fluids such as wound fluids (e.g. fibroblasts) may be treated by a peptide of the invention and re-introduced into the subject, according to protocols known in the art.

The FKE-containing peptides of the invention are herein demonstrated to have advantageous properties compared to other peptides such as FKD, in exerting an enhanced anti-inflammatory activity under inflammatory conditions. In addition, peptides having the amino acid FKE, such as those represented by Formula I of the invention, are particularly advantageous in promoting an anti-fibrotic cytokine profile, and in particular in up-regulating IL-10 secretion. Thus, in certain preferred embodiments of the methods of the invention, the use of peptides having the amino acid FKE, such as those represented by Formula I, may be favored, and especially in the methods employing enhancing IL-10 secretion, for inhibiting inflammation-induced fibrosis, treating or preventing a fibrotic disease, inhibiting scar formation and inhibiting inflammation in a subject identified as being afflicted with a disorder associated with an inappropriate or detrimental inflammatory response and fibrosis.

In addition, the use of sequences comprising the amino acids YKE, derived from the corresponding position in murine lactoferrin, is further contemplated in some embodiments of the invention. For example, the YKE-containing peptides may be useful for the treatment of chronic inflammatory diseases and conditions associated with adversely high IL-6 and/or TNF-α secretion. According to exemplary embodiments, peptides having the amino acid YKE, such as those represented by Formula II herein, may be used for inhibiting inflammation and for the treatment and prevention of peritonitis, mastitis, autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis), autoimmune hepatitis or rheumatoid arthritis. Each possibility represents a separate embodiment of the invention.

In other embodiments, the disease or disorder is other than multiple sclerosis, viral hepatitis, cancer or leptospirosis, wherein each possibility represents a separate embodiment of the invention. In other embodiments, the subject does not suffer simultaneously from multiple sclerosis, viral hepatitis, cancer or leptospirosis. In addition, without wishing to be bound by a single theory or mechanism of action, the peptides of the invention are not intended for vaccination against FKE or YKE-containing antigens, such as lactoferrin. Accordingly, typical pharmaceutical compositions comprising the peptides of the invention are not formulated as vaccines, and are not administered according to vaccination protocols. Such vaccines and protocols are known in the art, wherein the excipients (e g immunogenic adjuvants and/or carriers), administration routes, schedules and (high) antigen doses are determined so as to stimulate the production of antibodies and/or T cells specific to the administered antigen.

The present invention also provides any of the embodiments described above, where the method further comprises administering to the patient a therapeutically effective amount of at least a second agent, where the second agent is chosen from anti-inflammatory agents, anti-fibrotic agents, and anti-angiogenesis agents. In some of these embodiments, the second agent is chosen from a steroid, a NSAIDS (non-steroidal anti-inflammatory drugs), a chemotherapeutic agent as used in some auto-immune diseases, and an antibody or antisense agent directed to specific cytokines or to cytokine receptors or to other molecules which enhance inflammation and/or fibrosis. Yet in other embodiments, the methods of the invention contemplate the use of the synthetic peptide as described above as a sole active ingredient.

Nucleic Acid Constructs

In another embodiment, the invention relates to nucleic acid molecules, e.g. nucleic acid constructs, encoding the peptides of the invention (e.g. peptides of Formula I or II). In another embodiment there are provided pharmaceutical compositions comprising said nucleic acid constructs, optionally further comprising additional carriers, excipients or diluents. In another embodiment the invention relates to host cells comprising the constructs and pharmaceutical compositions comprising same.

In another embodiment, the invention relates to a pharmaceutical composition for use in treating or inhibiting inflammation in a subject in need thereof, comprising a nucleic acid construct encoding a peptide having the amino acid sequence FKE (SEQ ID NO: 1) and/or YKE (SEQ ID NO: 2). A nucleic acid construct encoding a peptide of the invention contains a nucleic acid sequence encoding said peptide, operably linked to a transcription regulating sequence. Accordingly, embodiments of the invention include a method of treating or inhibiting inflammation in a subject in need thereof, comprising administering to the subject a nucleic acid sequence encoding a peptide having the amino acid sequence FKE (SEQ ID NO: 1) and/or YKE (SEQ ID NO: 2), operably linked to a transcription regulating sequence.

The phrase "operably linked" refers to a nucleic acid sequence linked a to a transcription control sequence in a manner such that the molecule is able to be expressed when transfected (i.e., transformed, transduced, infected, or transfected) into a host cell. Transcription control sequences are sequences, which control the initiation, elongation, and termination of transcription. Particularly important transcription control sequences are those which control transcription initiation, such as promoter, enhancer, operator and repressor sequences.

The nucleic acid construct (also referred to herein as an "expression vector") of the present invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Constitutive promoters are promoter sequences which are active under most environmental conditions and most types of cells such as the cytomegalovirus (CMV) and Rous sarcoma virus (RSV). Inducible promoters include for example the tetracycline-inducible promoter.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine CMV, the long term repeat from various retroviruses such as murine leukemia virus, murine or RSV.

Polyadenylation sequences can also be added to the expression vector in order to increase RNA stability. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), and expression vectors containing regulatory elements from eukaryotic viruses such as pMSG, pAV009/A$^+$, pMT010/A$^+$, pMAMneo-5, and baculovirus pDSVE.

Various methods can be used to introduce the expression vector of the present invention into cells. Such methods are generally described in Sambrook et al., 2001, in and include, for example, stable or transient transfection, lipofection, electroporation and infection with recombinant viral vectors. In addition, see U.S. Pat. Nos. 5,464,764 and 5,487,992 for positive-negative selection methods. Exemplary in vivo nucleic acid transfer techniques include transfection with viral or non-viral constructs, such as adenovirus, lentivirus, Herpes simplex I virus, or adeno-associated virus (AAV) and lipid-based systems.

Conveniently, a nucleic acid construct comprising a nucleic acid sequence encoding a peptide of the invention operably linked to a transcription regulating sequence, may be administered to cells of the subject in the form of a nucleic acid composition, further comprising a pharmaceutically acceptable carrier. With respect to nucleic acid compositions, a "carrier" refers to any substance suitable as a vehicle for delivering a nucleic acid sequence of the present invention to a suitable in vivo site. As such, carriers can act as a pharmaceutically acceptable excipient of a therapeutic composition containing a nucleic acid molecule of the present invention. Preferred carriers are capable of maintaining a nucleic acid molecule of the present invention in a form that, upon arrival of the nucleic acid molecule to a cell, the nucleic acid molecule is capable of entering the cell and being expressed by the cell. Carriers of nucleic acid compositions of the present invention may include: (1) excipients or formularies that transport, but do not specifically target a nucleic acid molecule to a cell (referred to herein as non-targeting carriers); and (2) excipients or formularies that deliver a nucleic acid molecule to a specific site in an animal or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

ADDITIONAL EMBODIMENTS

According to additional embodiments, the FKE-containing peptides of the invention are herein demonstrated to have advantageous properties compared to other peptides such as FKD, in exerting an enhanced anti-inflammatory activity under inflammatory conditions. Yet, the results described herein further disclose that FKD, hitherto known as a pro-inflammatory peptide, also modulates TGF-β secretion. Thus, additional embodiments herein relate to novel uses for FKD-containing peptides, in inhibiting or modulating TGF-β expression, and in treating or preventing TGF-β-dependent disorders and other fibrotic disorders. In addition, the use of sequences comprising the amino acids YKE, derived from the corresponding position in murine lactoferrin, is further contemplated in some embodiments of the methods of the invention.

According to additional embodiments the invention relates to synthetic, recombinant or otherwise isolated peptides containing a plurality of "core" sequences selected from the group consisting of FKE, FKD and/or YKE, e.g. 2-5 core sequences, which may be flanked by one or more linker sequences of 1-7 aa. According to these embodiments, the core sequences are flanked by linker sequences containing the amino acids alanine (A) and/or glycine (G), preferably consisting of the amino acids alanine and/or glycine. The peptides according to these embodiments may further contain additional amino acids and/or chemical derivatizing groups. These peptides explicitly exclude known peptides such as those described in the Background section herein.

Certain additional exemplary embodiments of the invention are described below.

1. A method for inhibiting inflammation in a subject in need thereof, comprising administering to the subject an isolated peptide having the amino acid sequence FKE (SEQ ID NO: 1), thereby inhibiting inflammation in said subject.
2. The method of clause 1, comprising, prior to administering the peptide, identifying said subject as being afflicted with a disorder associated with an inappropriate or detrimental inflammatory response.
3. The method of clause 2, wherein the disorder is associated with fibrosis.
4. The method of clause 2, wherein said disorder is a chronic inflammatory disease.
5. The method of clause 4, wherein said disorder is an autoimmune disease.
6. The method of clause 5, wherein the disease is selected from the group consisting of multiple sclerosis, autoimmune neuritis, SLE, psoriasis, IDDM, Sjogren's disease, thyroid disease, myasthenia gravis, sarcoidosis, autoimmune uveitis, inflammatory bowel disease, autoimmune hepatitis or rheumatoid arthritis.
7. The method of clause 3, wherein said disorder is associated with fibrosis in the skin, in the lung, in the liver, in the kidney, of the central nervous system, in bone or bone marrow, in the cardiovascular system, in an endocrine organ or in the gastro-intestinal system.
8. The method of clause 7 used for inhibiting lung fibrosis or fibrotic disorders of the liver.
9.

The method of clause 3, wherein said disorder is a fibrotic disease selected from the group consisting of cirrhosis of the liver, constrictive pericarditis, Dupuytren's disease of the hand, plantar fibrosis of the foot, COPD, emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, CGD, chronic diabetic wounds and fibrosis resulting after surgery.
10. The method according to any one of clauses 1-9, wherein said disorder is IL-10-dependent.
11. The method of clause 10, wherein said disorder is associated with increased TGF-β levels and inhibited or alleviated by increased IL-10 levels.
12. A method for inducing or enhancing IL-10 secretion in a subject in need thereof, comprising administering to the subject an isolated peptide having the amino acid sequence FKE, thereby inducing or enhancing IL-10 secretion in said subject.
13. A method for treating an inflammatory disease in a subject in need thereof, comprising identifying the subject as suffering from the disease, and administering to said subject an isolated peptide having the amino acid sequence FKE (SEQ ID NO: 1), thereby treating said inflammatory disease in said subject.
14. A method for inhibiting inflammation-induced fibrosis in a subject in need thereof, comprising identifying the subject as suffering from or at risk of developing inflammation-induced fibrosis, and administering to said subject an isolated peptide having the amino acid sequence FKE (SEQ ID NO: 1), thereby inhibiting said inflammation-induced fibrosis in said subject.
15. A method for treating or preventing a fibrotic disease in a subject in need thereof, comprising identifying the subject as suffering from or at risk of developing the fibrotic disease, and administering to said subject an isolated peptide having the amino acid sequence FKE (SEQ ID NO: 1), thereby treating or preventing said inflammation-induced fibrosis in said subject.
16. A method for inhibiting scar formation in a subject in need thereof, comprising administering to said subject an isolated peptide having the amino acid sequence FKE (SEQ ID NO: 1), thereby inhibiting scar formation in said subject.
17. A method for treating an IL-10 dependent condition in a subject in need thereof, comprising identifying the subject as suffering from the condition, and administering to said subject an isolated peptide having the amino acid sequence FKE, thereby treating said condition in said subject.
18. The method according to any one of clauses 12-17 wherein the subject is afflicted with a disease or disorder associated with fibrosis.
19. The method according to any one of clauses 12-17 wherein the subject is afflicted with a chronic inflammatory disease.
20. The method according to any one of clauses 12-17 wherein the subject is afflicted with an autoimmune disease.
21. The method according to clause 20 wherein the disease is selected from the group consisting of multiple sclerosis, autoimmune neuritis, SLE, psoriasis, IDDM, Sjogren's disease, thyroid disease, myasthenia gravis, sarcoidosis, autoimmune uveitis, inflammatory bowel disease, autoimmune hepatitis or rheumatoid arthritis.
22. The method according to clause 18 wherein said disorder is associated with fibrosis in the skin, in the lung, in the liver, in the kidney, of the central nervous system, in bone or bone marrow, in the cardiovascular system, in an endocrine organ or in the gastro-intestinal system.
23. The method according to any one of clauses 12-17 used for inhibiting lung fibrosis or fibrotic disorders of the liver.
24. The method according to clauses 18, wherein said disorder is a fibrotic disease selected from the group consisting of cirrhosis of the liver, constrictive pericarditis, Dupuytren's disease of the hand, plantar fibrosis of the foot, COPD, emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, CGD, chronic diabetic wounds and fibrosis resulting after surgery.
25. The method of clause 12 that induces or enhances IL-10 secretion from macrophages in said subject.

26. The method according to any one of clauses 12-17 wherein the subject is afflicted with a disease or disorder that is IL-10-dependent.
27. The method according to any one of clauses 12-17 wherein the subject is afflicted with a disease or disorder associated with increased TGF-β levels and inhibited or alleviated by increased IL-10 levels.
28. A method according to any one of clauses 1-27 wherein said peptide is 3-20 amino acids in length.
29. A method according to any one of clauses 1-28 wherein said peptide contains a plurality of FKE sequences.
30. A method according to clause 29 wherein said peptide contains 2-5 repeated FKE sequences.
31. A method according to clause 29 wherein said FKE sequences are flanked by linker sequences of 1-7 amino acids.
32. The method of clause 31 wherein said linker sequences contain the amino acids alanine and/or glycine.
33. The method of clause 31 wherein said linker sequences consist of the amino acids alanine and/or glycine.
34. A method according to any one of clauses 1-33 wherein said peptide further comprises a YKE (SEQ ID NO: 2) sequence.
35. A method according to any one of clauses 1-33 wherein said peptide does not contain an FKD (SEQ ID NO: 3) sequence.
36. A method according to any one of clauses 1-27 wherein said peptide is SEQ ID NO: 1, optionally chemically derivatized at the N- and/or C-terminus.
37. A method according to any one of clauses 1-36 wherein said subject is human or bovine.
38. A method according to any one of clauses 1 and 12-17, wherein said peptide is administered topically.
39. A method according to any one of clauses 1-38 wherein said peptide is not administered in a vaccination protocol or formulation.
40. A synthetic, recombinant or otherwise isolated peptide of 3-19 amino acids in length, of the following Formula I:

$$X^1-[(S^1)(FKE)(S^2)]_n-X^2 \qquad (I)$$

wherein: n is an integer of 1-5; $X^1$ is an amino acid, a peptide of 2-7 amino acids other than YR and LDH, a chemical derivatizing group or is absent; $S^1$ is an amino acid, a spacer of 2-7 amino acids comprising a plurality of A and/or G residues, or may be absent; wherein when n=1, $X^1$ is absent and $S^1$ is an amino acid, $S^1$ is not K or R; $S^2$ is an amino acid, a spacer of 2-7 amino acids comprising a plurality of A and/or G residues, or may be absent; wherein when n=1, $X^2$ is absent and $S^2$ is an amino acid, $S^2$ is not V, K or R; $X_2$ is an amino acid, a peptide of up to 7 amino acids, a chemical derivatizing group or is absent; wherein when n=1 and $S^2$ is absent, $X^2$ is not HWR, LEG, CTV, CHL, CHLA or HLA.

41. The peptide of clause 40, wherein $X^1$ is not RGD, K, R, Q, Y, SQI, IN or VDA.
42. The peptide of clause 39, wherein $X^1$ does not contain RGD, K, R, Q, Y, SQI, IN or VDA.
43. The peptide of clause 40, wherein $S^1$ is not K, R, Q, Y, S or T.
44. The peptide of clause 40, wherein $S^2$ is not V, K, R, Q, H, I, or L.
45. The peptide of clause 40, wherein $S^1$ and/or $S^2$ are individually A, G, or spacer peptides consisting of A and/or G residues.
46. The peptide of clause 40, wherein $X^2$ is not HWR, LEG, CTV, RGD, K, DI, ST, VT, Y, LA, CHL, CHLA or HLA.

47. The peptide of clause 40, wherein $X^2$ does not contain HWR, LEG, CTV, RGD, K, DI, ST, VT, Y, LA, CHL, CHLA or HLA.
48. The peptide of clause 40, which peptide is 3-10 amino acids in length.
49. The peptide of clause 40 wherein said peptide is SEQ ID NO: 1, optionally chemically derivatized at the N- and/or C-terminus.
50. The peptide of clause 40, comprising one or more YKE sequences.
51. The peptide of clause 40, which does not comprise an FKD sequence.
52. The peptide of clause 40, wherein n is an integer of 2-5.
53. The peptide of clause 40, which is capable of inducing IL-10 secretion from human macrophages.
54. A pharmaceutical composition containing an effective amount of a peptide of the previous clauses and one or more pharmaceutically accepted carriers, excipients or diluents.
55. A synthetic, recombinant or otherwise isolated peptide of 3-20 amino acids in length, of the following Formula I:

$$X^1-[(S^1)(FKE)(S^2)]_n-X^2 \qquad (I)$$

wherein: n is an integer of 1 to 5; $X^1$ is an amino acid, a peptide of 2 to 7 amino acids other than YR and LDH, a chemical derivatizing group or is absent; $S^1$ is an amino acid, a spacer of 2 to 7 amino acids comprising a plurality of A and/or G residues, or may be absent; wherein when n=1, $X^1$ is absent and $S^1$ is an amino acid, $S^1$ is not K or R; $S^2$ is an amino acid, a spacer of 2 to 7 amino acids comprising a plurality of A and/or G residues, or may be absent; wherein when n=1, $X^2$ is absent and $S^2$ is an amino acid, $S^2$ is not V, K or R; $X_2$ is an amino acid, a peptide of 2 to 7 amino acids, a chemical derivatizing group or is absent; wherein when n=1 and $S^2$ is absent, $X^2$ is not HWR, LEG, LEGWEP, CTV, CTVEY, CTVEYEL, CHL, CHLA or HLA.

56. The peptide of clause 55, wherein $X^1$ is not RGD, K, R, Q, Y, SQI, IN, H, DH, SLDH, AT or VDA, or wherein $X^1$ does not contain RGD, K, R, Q, Y, SQI, IN, H, DH, SLDH, AT or VDA.
57. The peptide of clause 55, wherein $S^1$ is not K, R, Q, Y, S or T, and/or wherein $S^2$ is not V, K, R, Q, H, I, or L.
58. The peptide of clause 55, wherein $S^1$ and/or $S^2$ are individually A, G, or spacer peptides consisting of A and/or G residues.
59. The peptide of clause 55, wherein $X^2$ is not HWR, LEG, LEGWEP, CTV, CTVEY, CTVEYEL, RGD, K, DI, KDI, ST, VT, Y, LA, CHL, CHLA or HLA, or wherein $X^2$ does not contain HWR, LEG, LEGWEP, CTV, CTVEY, CTVEYEL, RGD, K, DI, KDI, ST, VT, Y, LA, CHL, CHLA or HLA.
60. The peptide of clause 55, which peptide is 3-10 amino acids in length.
61. The peptide of clause 55 wherein said peptide is SEQ ID NO: 1, or a peptide of SEQ ID NO: 1 which is chemically derivatized at the N- and/or C-terminus.
62. The peptide of clause 55, comprising one or more YKE sequences.
63. The peptide of clause 55, which does not comprise an FKD sequence.
64. The peptide of clause 55, wherein n is an integer of 2-5.
65. The peptide of clause 55, which induces IL-10 secretion from human macrophages.
66. A pharmaceutical composition containing an effective amount of a peptide according to any one of clauses 55-65 and one or more pharmaceutically accepted carriers, excipients or diluents.

67. A pharmaceutical composition according to clause 66, for use in inducing or enhancing IL-10 secretion in a subject in need thereof.

68. A pharmaceutical composition according to clause 66, for use in treating an inflammatory disease in a subject in need thereof.

69. The composition according to clause 68 wherein the disease is selected from the group consisting of peritonitis, mastitis, multiple sclerosis, autoimmune neuritis, SLE, psoriasis, IDDM, Sjogren's disease, thyroid disease, myasthenia gravis, sarcoidosis, autoimmune uveitis, inflammatory bowel disease, autoimmune hepatitis and rheumatoid arthritis.

70. A pharmaceutical composition according to clause 66, for use in inhibiting inflammation-induced fibrosis in a subject in need thereof.

71. The composition of clause 70 used for inhibiting lung fibrosis or fibrotic disorders of the liver.

72. A pharmaceutical composition according to clause 66, for use in treating or preventing a fibrotic disease in a subject in need thereof.

73. The composition according to clause wherein said disease is associated with fibrosis in the skin, in the lung, in the liver, in the kidney, of the central nervous system, in bone or bone marrow, in the cardiovascular system, in an endocrine organ or in the gastro-intestinal system.

74. The composition according to clause 72 wherein said disease is a fibrotic disease selected from the group consisting of cirrhosis of the liver, constrictive pericarditis, Dupuytren's disease of the hand, plantar fibrosis of the foot, COPD, emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, CGD, chronic diabetic wounds and fibrosis resulting after surgery.

75. A pharmaceutical composition according to clause 66, for use in inhibiting scar formation in a subject in need thereof.

76. A synthetic, recombinant or otherwise isolated peptide of 3-20 amino acids in length, of the following Formula II:

$$X^1-[(S^1)(YKE)(S^2)]_n-X^2 \quad (II)$$

wherein: n is an integer of 1-5; $X^1$ is an amino acid, a peptide of 2-7 amino acids other than RR, MDIDP, and KKNWIQ, a chemical derivatizing group or is absent; $S^1$ is an amino acid, a spacer of 2-7 amino acids comprising a plurality of A and/or G residues, or may be absent; wherein when n=1, $X^1$ is absent and $S^1$ is an amino acid, $S^1$ is not Y or E; $S^2$ is an amino acid, a spacer of 2-7 amino acids comprising a plurality of A and/or G residues, or may be absent; wherein when n=1, $X^2$ is absent and $S^2$ is an amino acid, $S^2$ is not Y; $X_2$ is an amino acid, a peptide of up to 7 amino acids, a chemical derivatizing group or is absent; wherein when n=1 and $S^2$ is absent, $X^2$ is not KEK.

77. The peptide of clause 76, wherein $X^2$ is not Y, ERHNK or KEK, or wherein $S^1$ is not Y or E.

78. The peptide of clause 76, wherein said peptide is SEQ ID NO: 2, or a peptide of SEQ ID NO: 2 which is chemically derivatized at the N- and/or C-terminus.

79. A pharmaceutical composition containing an effective amount of a peptide according to any one of clauses 76-78 and one or more pharmaceutically accepted carriers, excipients or diluents.

80. A pharmaceutical composition according to clause 79, for use in treating an inflammatory disease in a subject in need thereof.

81. The composition of clause 80 wherein the disease is selected from the group consisting of peritonitis, mastitis, autoimmune neuritis, SLE, psoriasis, IDDM, Sjogren's disease, thyroid disease, myasthenia gravis, sarcoidosis, autoimmune uveitis, inflammatory bowel disease, autoimmune hepatitis and rheumatoid arthritis.

82. A method for inhibiting inflammation in a subject in need thereof, comprising administering to, or expressing in cells of the subject, a synthetic, recombinant or isolated peptide having the amino acid sequence FKE (SEQ ID NO: 1), thereby inhibiting inflammation in said subject.

83. The method of clause 82, comprising, prior to administering the peptide, identifying said subject as being afflicted with a disorder associated with an inappropriate or detrimental inflammatory response.

84. The method of clause 83, wherein the disorder is associated with fibrosis, or wherein said disorder is an autoimmune disease or another chronic inflammatory disease.

85. The method of clause 84, wherein the disease is selected from the group consisting of peritonitis, mastitis, multiple sclerosis, autoimmune neuritis, SLE, psoriasis, IDDM, Sjogren's disease, thyroid disease, myasthenia gravis, sarcoidosis, autoimmune uveitis, inflammatory bowel disease, autoimmune hepatitis and rheumatoid arthritis.

86. The method of clause 83, wherein said disorder is associated with fibrosis in the skin, in the lung, in the liver, in the kidney, of the central nervous system, in bone or bone marrow, in the cardiovascular system, in an endocrine organ or in the gastro-intestinal system.

87. The method of clause 86 used for inhibiting lung fibrosis or fibrotic disorders of the liver.

88. The method of clause 82, for inhibiting inflammation-induced fibrosis in said subject.

89. The method of clause 88, wherein the fibrosis is associated with a fibrotic disease selected from the group consisting of cirrhosis of the liver, constrictive pericarditis, Dupuytren's disease of the hand, plantar fibrosis of the foot, COPD, emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, CGD, chronic diabetic wounds and fibrosis resulting after surgery.

90. The method of clause 82, for inhibiting scar formation in said subject.

91. The method according to clause 90, wherein said disorder is IL-10-dependent.

92. The method of clause 91, wherein said disorder is associated with increased TGF-β levels and is inhibited or alleviated by increased IL-10 levels.

93. The method of clause 82, wherein said peptide is 3-20 amino acids in length.

94. The method of clause 82, wherein said peptide contains a plurality of FKE sequences.

95. The method of clause 94 wherein said peptide contains 2-5 repeated FKE sequences.

96. The method of clause 94 wherein said FKE sequences are flanked by linker sequences of 1-7 amino acids.

97. The method of clause 95, wherein said FKE sequences are flanked by linker sequences of 1-7 amino acids, wherein said linker sequences contain the amino acids alanine and/or glycine, or wherein said linker sequences consist of the amino acids alanine and/or glycine.

98. The method of clause 82 wherein said peptide further comprises one or more YKE (SEQ ID NO: 2) sequences.

99. The method of clause 82 wherein said peptide does not contain an FKD (SEQ ID NO: 3) sequence.

100. The method of clause 82 wherein said peptide is SEQ ID NO: 1, or a peptide of SEQ ID NO: 1 which is chemically derivatized at the N- and/or C-terminus.

101. The method of clause 82, wherein said peptide is administered topically.

The following examples are presented in order to more fully illustrate some embodiments of the invention. They should, in no way be construed, however, as limiting the broad scope of the invention.

EXAMPLES

Example 1

U937 monocytic cells were cultured in 1 ml culture media (RPMI 1640, Biological industries, Beit Haemek), supplemented with 10% Fetal Calf Serum (FCS), 1% pen strep (PS) and 0.04% β-mercaptoethanol) and seeded in 24 well plates (250,000 cells/well). The monocytes underwent differentiation to macrophages with PMA (50 ng/ml) for 48 Hours in a humidified atmosphere (7.5% $CO_2$ at 37° C.). Then the cells were washed using preheated (37° C.) culture medium and synthetic peptides (FKE, SEQ ID NO: 1, or FKD, SEQ ID NO: 3, 0.1-1000 μM) were added to the cells for 24-48 hours. After 24 hours, untreated or peptide-treated cells were activated with lipopolysaccharide (LPS-stimulated, 100 ng/ml for 24 hours). After the indicated incubations, cell free supernatants were collected and their content of IL-10, TGF-β and IL-6 was determined by standard ELISA.

Figure 1B:
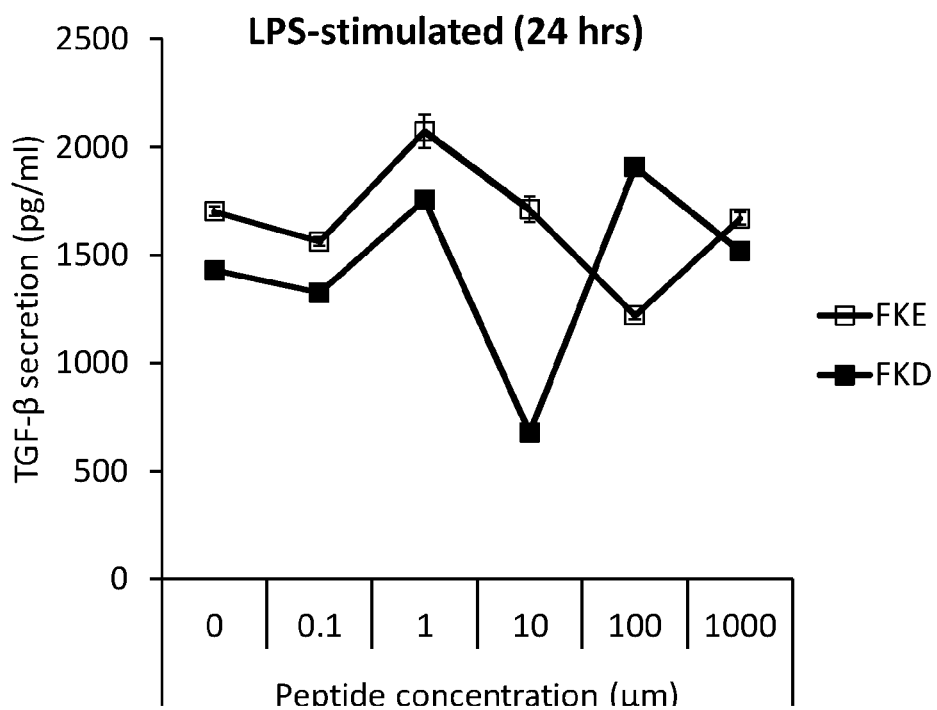
Figure 1C:
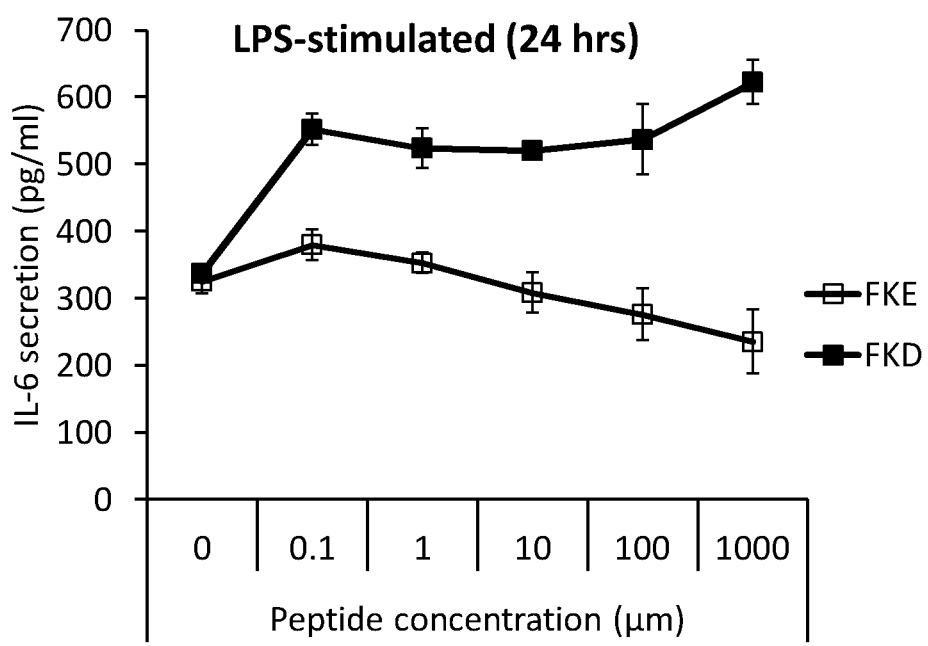
Figure 2A:
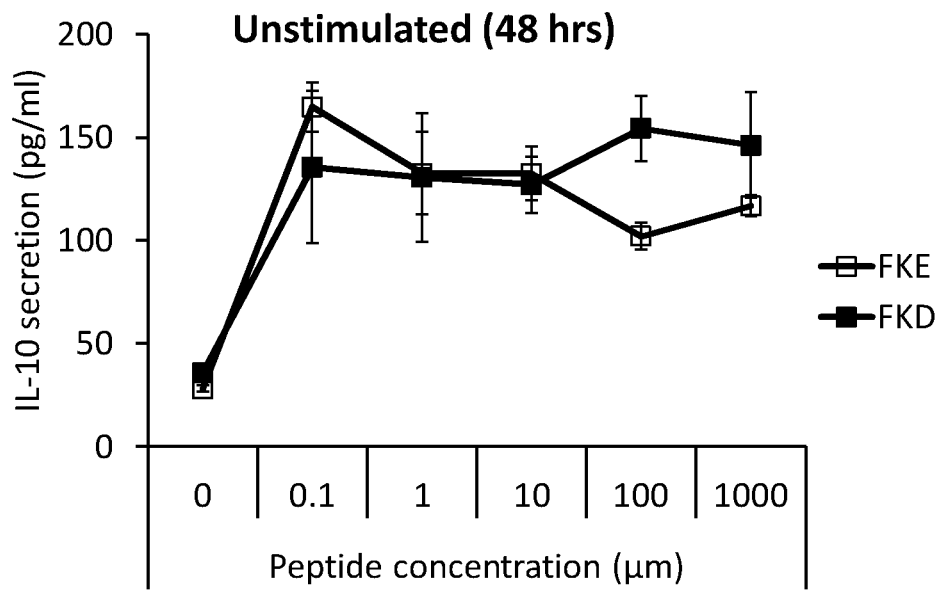
FIG. 2. Human macrophages were treated with the indicated concentrations of FKE (open squares) or FKD (closed squares) peptides for 48 hrs. Next, culture supernatants were collected and their content of IL-10, TGF-β and IL-6 (FIGS. 2A, 2B and 2C, respectively) was determined by standard ELISA.
Figure 2B:
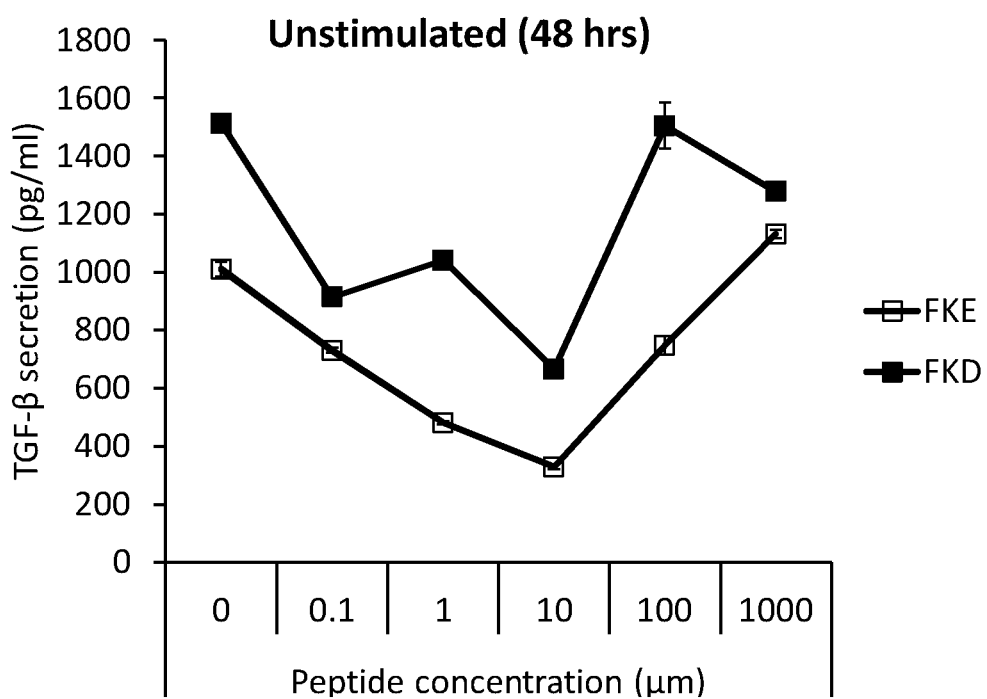
Figure 2C:
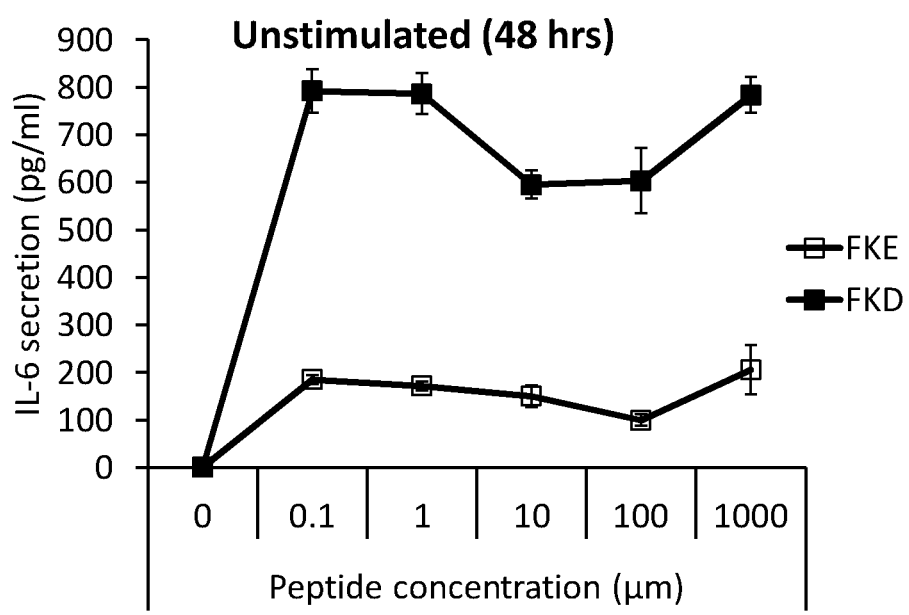
Figure 3A:
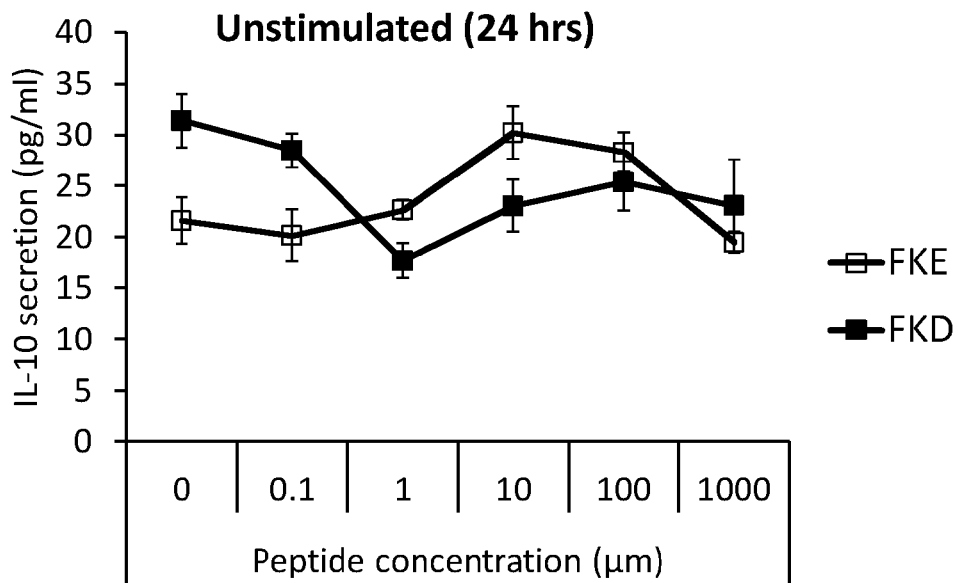
FIG. 3. Human macrophages were treated with the indicated concentrations of FKE (open squares) or FKD (closed squares) peptides for 24 hrs. Next, culture supernatants were collected and their content of IL-10, TGF-β and IL-6 (FIGS. 3A, 3B and 3C, respectively) was determined by standard ELISA.
Figure 3B:
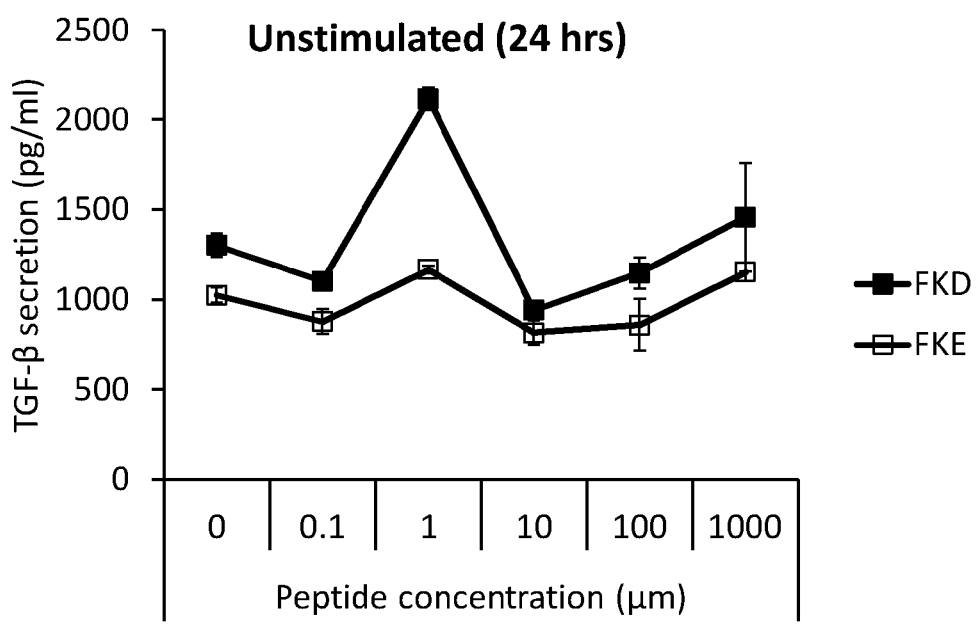
Figure 3C:
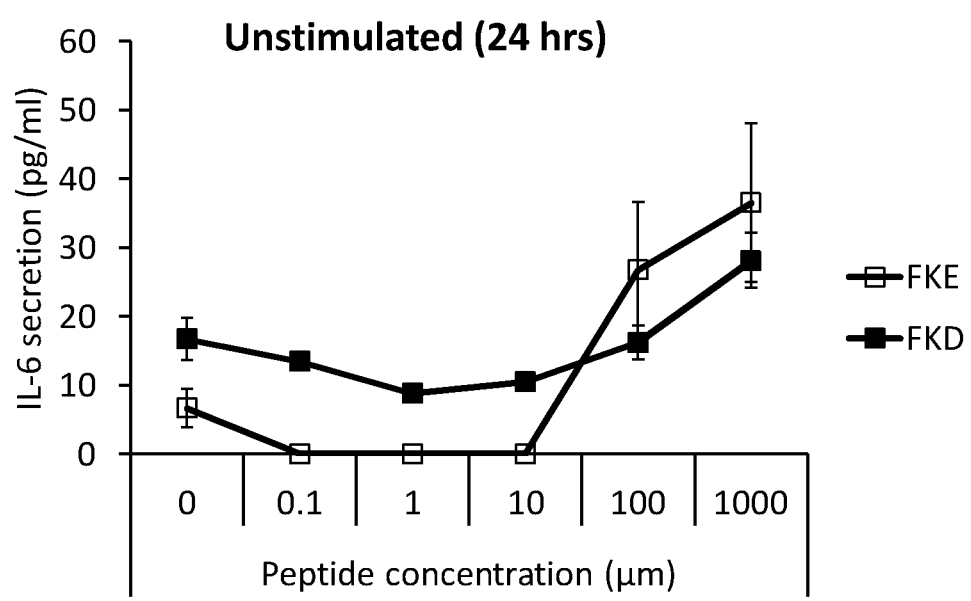
Figure 4A:
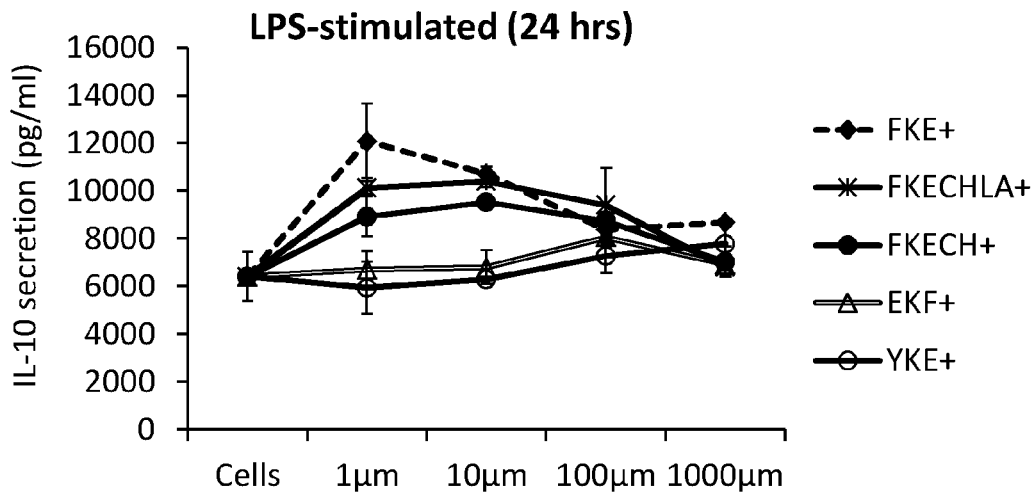
FIG. 4. Human macrophages were treated with the indicated concentrations of the following peptides for 24 hrs: FKE (closed diamonds, dashed line), FKECHLA (asterisks, solid line), FKECH (closed circles, solid line), EKF (open triangles, double line) or YKE (open circles, solid line). "Cells" indicates untreated macrophage cells, with no added peptide. Then, the cells were treated with LPS and incubation was continued for additional 24 hrs. Next, culture supernatants were collected and their content of IL-10, TGF-β, IL-6 and TNF-α (FIGS. 4A, 4B, 4C and 4D, respectively) was determined by standard ELISA.
Figure 4B:
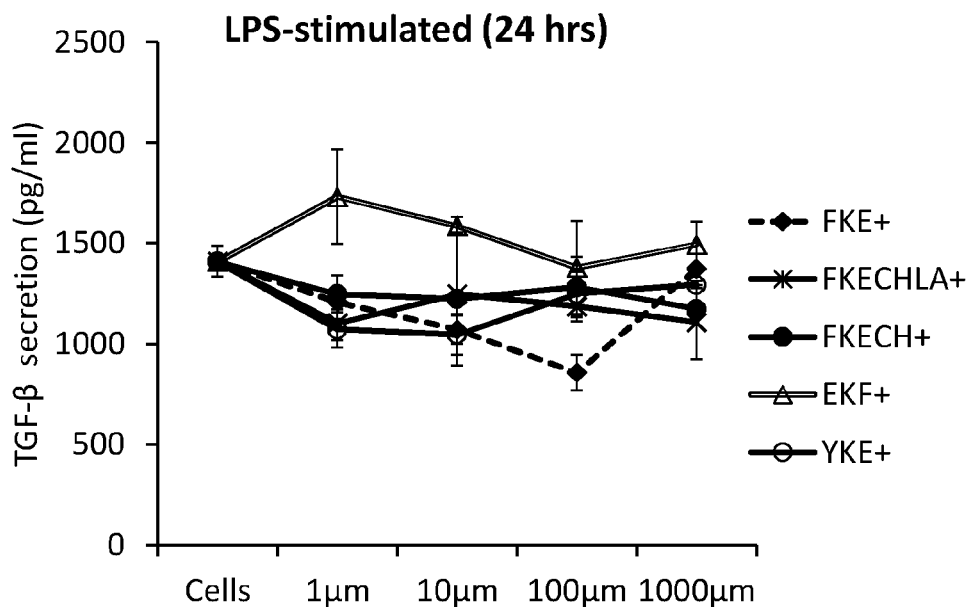
Figure 4C:
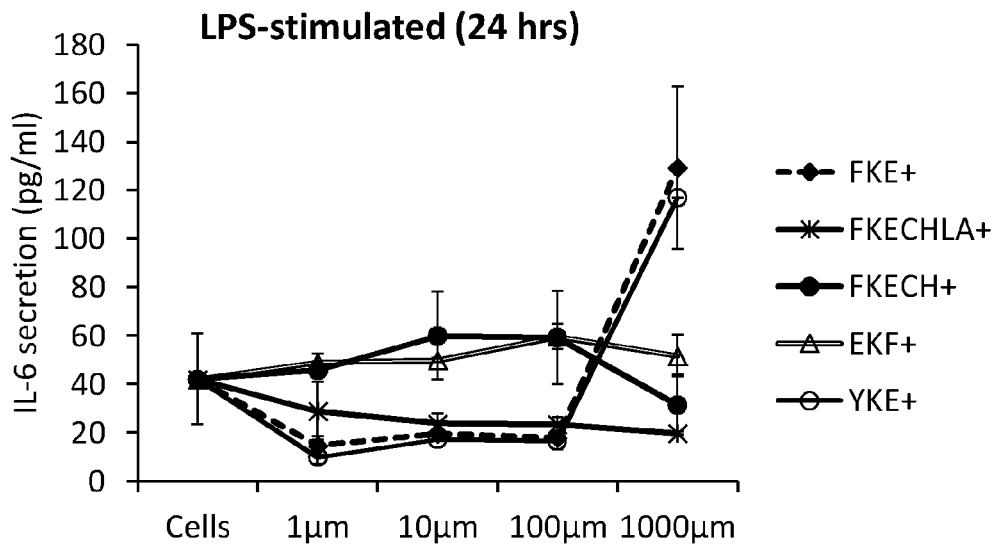
Figure 4D:
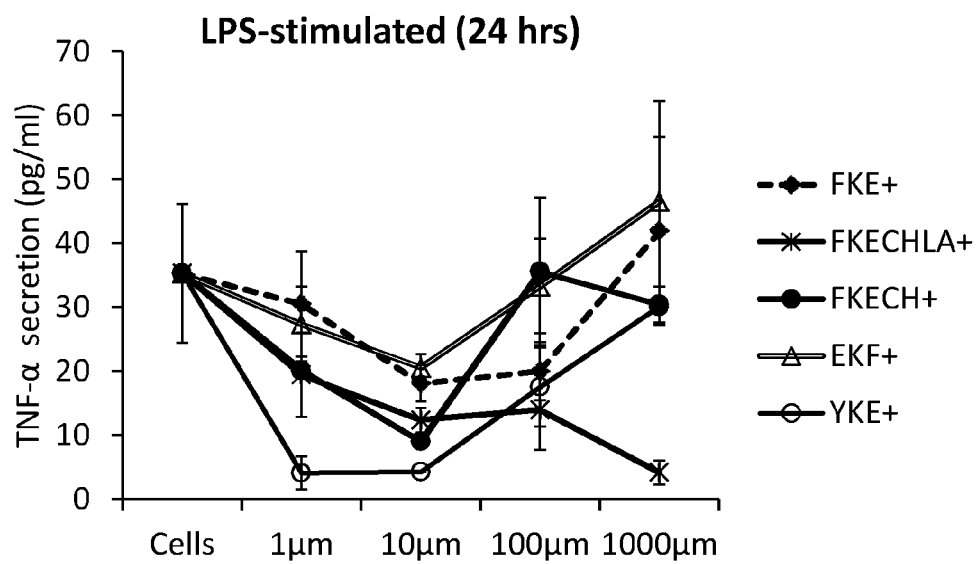

The results are presented in FIGS. 1-3 and summarized in Table 1 below (effect considered significant if ±30% of control):

was increased following incubation with FKE and decreased following incubation with FKD; IL-6 secretion was increased following incubation with FKD but not FKE.

Example 2

U937 monocytic cells were cultured and underwent differentiation to macrophages as described above in Example 1. The cells were then incubated for 24 hrs in the presence of synthetic peptides, at 1-1000 μM: FKE (SEQ ID NO: 1), FKECHLA (SEQ ID NO: 21), FKECH (SEQ ID NO: 4), EKF or YKE (SEQ ID NO: 2). Control cells were left untreated. After 24 hours, untreated or peptide-treated cells were activated with lipopolysaccharide (LPS, 100 ng/ml for 24 hours). Following activation with LPS, cell free supernatants were collected and their content of IL-10, TGF-β, IL-6 and TNF-α was determined by standard ELISA. The results are presented in FIG. 4.

As can be seen from the results, the FKE peptide at low concentrations (1-10 μM) induces IL-10 secretion and inhibits TNF-α, IL-6, and TGF-β secretion. The control reversed EKF peptide did not reproduce these effects except for a moderate inhibition of TNF-α. The YKE peptide reproduced these effects for IL-6 and TNF-α (with a better inhibition of TNF-α at the low concentration) but did not affect IL-10 secretion. The FKECHLA peptide reproduced the effects of the FKE peptide on IL-6 and TNF-α, and to a lesser extent on IL-10 and TGF-β but notably did not show a bell-shaped response for IL-6 and TNF-α. The FKECH peptide was less active than FKE on IL-6, IL-10 and TGF-β, but showed a pronounced activity in inhibiting TNF-α.

Example 3

The mouse model of bleomycin-induced dermal fibrosis is used to evaluate anti-inflammatory and anti-fibrotic effects of the peptides in vivo, as described in Krönke et al., 2012, *Ann Rheum Dis.*, 71(6):1081-7. Skin fibrosis is induced in 6-week-old C57Bl/6 mice by local injections of bleomycin

TABLE 1

| | cytokine secretion by macrophages | | | | | |
| --- | --- | --- | --- | --- | --- | --- |
| | Peptide | | | | | |
| | FKE | FKD | FKE | FKD | FKE | FKD |
| | | | Activation | | | |
| | Non-stimulated | Non-stimulated | Non-stimulated | Non-stimulated | LPS-stimulated | LPS-stimulated |
| | | | Incubation | | | |
| Cytokine | (24 hrs) | (24 hrs) | (48 hrs) | (48 hrs) | (24 hrs) | (24 hrs) |
| IL-10 | Increase (max at 10 μM) | Decrease (max at 1 μM) | Increase (max at 0.1 μM) | Increase (max at 1000 μM) | Increase (max at 1 μM) | Decrease (max at 100 μM) |
| TGF-β | No effect | Increase (max at 1 μM) | Decrease (max at 10 μM) | Decrease (max at 10 μM) | Decrease (max at 100 μM) | Decrease (max at 10 μM) |
| IL-6 | Decrease (at 1 μM), Increase (at 1000 μM) | Decrease (at 1 μM), Increase (at 1000 μM) | Increase (starts at 0.1 μM) | Increase (4 fold of FKE, starts at 0.1 μM) | No Increase | Increase (all conc.) |

As can be seen from the results, the FKE peptide at low concentrations (1-10 μM) induces IL-10 secretion and inhibits TGF-β secretion. The observed effects on IL-6 (in non-stimulated cells) change with concentration and time (from decrease to increase). The FKD peptide exerted less anti-fibrotic and more pro-inflammatory effects. Notably, under inflammatory conditions induced by LPS, IL-10 secretion for 4 weeks. 100 μl of bleomycin dissolved in 0.9% sodium chloride (NaCl) at a concentration of 0.5 mg/ml is administered every other day b y subcutaneous injections in defined areas of 1 $cm^2$ at the upper back. Bleomycin is administered alone or concomitantly with a synthetic peptide at a concentration of 50 micromolar (μM). Subcutaneous injections of 100 μl 0.9% NaCl are used as controls.

Each group (bleomycin only, bleomycin+peptide and 0.9% NaCl) consists of six to eight mice.

Mice are killed by cervical dislocation after 4 weeks, and their skin architecture and dermal thickness are evaluated. The dermal thickness is analyzed at 100-fold magnification by measuring the distance between the epidermal-dermal junction and the dermal subcutaneous fat junction at three sites from lesional skin of each mouse. Collagen fibers are visualized by Masson's trichrome staining and analyzed at 1000-fold magnification. The number of myofibroblasts is determined, by using immunohistochemistry for α-smooth muscle actin to identify the myofibroblasts.

The following peptides are evaluated: FKE (SEQ ID NO: 1), Acetyl-FKE-amide (SEQ ID NO: 7), FKECH (SEQ ID NO: 4), FKECHLA (SEQ ID NO: 21), YKE (SEQ ID NO: 2), FKEAAAAAFKEAAAAAFKEAAAAAF-KEAAAAAFKE (SEQ ID NO: 5), FKEGGGGGFKEG-GGGGFKEGGGGGFKEGGGGGFKE (SEQ ID NO: 6), and Acetyl-AAAAAFKEAAAAAFKEAAAAAF-KEAAAAA-amide (SEQ ID NOs: 8, respectively). The peptides FKD (SEQ ID NO: 3) and EKF are tested for comparison.

Example 4

Anti-inflammatory effect of the peptides in vivo is further evaluated in a mouse model of peritonitis. Male C57BL/6 mice (6-8 wk)) are injected intraperitoneally (I.P.) with zymosan A (1 mg). 48 hrs following zymosan A injection, the mice are injected I.P with a synthetic peptide at a concentration of 50 micromolar (µM) or left untreated. Each group (zymosan A only, and zymosan A+peptide) consists of 4 to 6 mice.

66-72 hrs following zymosan A injection the mice are euthanized with $CO_2$ and peritoneal exudates are collected by lavaging with 5 ml of sterile saline. The peritoneal exudates are evaluated for their content of TGF-β. Alternatively, macrophages are isolated and stimulated with LPS (16 hrs), and the levels of IL-10, TGF-β, IL-6, and TNF-α in supernatants are determined by standard ELISA. The peptides of SEQ ID NOs: 1-8 and 21 are evaluated, with the peptide EKF further tested for comparison.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating or inhibiting inflammation in a subject in need thereof identified as being afflicted with a disorder associated with an inappropriate or detrimental inflammatory response, comprising administering to the subject a pharmaceutical composition comprising a synthetic or recombinant peptide consisting of FKE (SEQ ID NO: 1), or 2-5 repeated FKE sequences, wherein said peptide may be chemically derivatized at the N- and/or C-terminus by non-peptide stabilizing chemical groups, and wherein said composition is used for inhibiting inflammation-induced fibrosis in said subject, or for inhibiting scar formation in said subject.

2. The method of claim 1, wherein said disorder is associated with fibrosis in the skin, in the lung, in the liver, in the kidney, of the central nervous system, in bone or bone marrow, in the cardiovascular system, in an endocrine organ or in the gastro-intestinal system, or wherein said composition is used for inhibiting inflammation-induced fibrosis associated with a fibrotic disease selected from the group consisting of cirrhosis of the liver, constrictive pericarditis, Dupuytren's disease of the hand, plantar fibrosis of the foot, chronic obstructive pulmonary disease (COPD), emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, chronic granulomatous disease (CGD), chronic diabetic wounds and fibrosis resulting after surgery.

3. The method of claim 1, wherein said disorder is IL-10-dependent, and associated with increased TGF-β levels and inhibited by increased IL-10 levels, or wherein said peptide is formulated for topical administration.

4. The method of claim 1 wherein said peptide is SEQ ID NO: 1, optionally chemically derivatized at the N- and/or C-terminus.

5. The method of claim 2, wherein said disorder is associated with fibrosis in the liver.

6. A method for inhibiting inflammation-induced fibrosis and scar formation in a subject in need thereof, comprising the step of administering to the subject a pharmaceutical composition comprising the peptide consisting of FKE (SEQ ID NO: 1), which may be chemically derivatized at the N- and/or C-terminus by non-peptide stabilizing chemical groups, thereby inhibiting inflammation-induced fibrosis and scar formation in said subject.

7. The method of claim 6, wherein said subject is identified as being afflicted with a disorder associated with an inappropriate or detrimental inflammatory response and fibrosis.

8. The method of claim 7, wherein the disorder is associated with fibrosis in the skin, in the lung, in the liver, in the kidney, of the central nervous system, in bone or bone marrow, in the cardiovascular system, in an endocrine organ or in the gastro-intestinal system.

9. The method of claim 7, wherein said composition is used for inhibiting inflammation-induced fibrosis associated with a fibrotic disease selected from the group consisting of cirrhosis of the liver, constrictive pericarditis, Dupuytren's disease of the hand, plantar fibrosis of the foot, chronic obstructive pulmonary disease (COPD), emphysema, idiopathic pulmonary fibrosis, nephrogenic fibrosis, endometrial fibrosis, perineural fibrosis, myocardial fibrosis, acute lung injury, renal interstitial fibrosis, scleroderma, cystic fibrosis, pancreatic fibrosis, keloid, secondary fibrosis in the gastrointestinal tract, hypertrophic burn scars, myocardial fibrosis, Alzheimer's disease, retinal detachment inflammation, chronic granulomatous disease (CGD), chronic diabetic wounds and fibrosis resulting after surgery.

10. The method of claim 7, wherein said disorder is IL-10-dependent, and associated with increased TGF-β levels and inhibited by increased IL-10 levels.

11. The method of claim 6, wherein said composition is formulated for topical administration.

12. The method of claim 6, wherein said peptide is chemically derivatized by C' amidation and/or N' acetylation.

* * * * *